(12) United States Patent
Yarmush et al.

(10) Patent No.: US 9,387,152 B2
(45) Date of Patent: Jul. 12, 2016

(54) BLOOD SUBSTITUTES AND USES THEREOF

(75) Inventors: Martin L. Yarmush, Newton, MA (US); Eric Yang, Cambridge, MA (US); Tali Konry, Boston, MA (US); Erkin Seker, Davis, CA (US); Dhruv Sarin, Shrewsbury, MA (US); Prakash Rai, Quincy, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 7 days.

(21) Appl. No.: 13/805,245

(22) PCT Filed: Jun. 28, 2011

(86) PCT No.: PCT/US2011/042213
§ 371 (c)(1), (2), (4) Date: Aug. 7, 2013

(87) PCT Pub. No.: WO2012/006101
PCT Pub. Date: Jan. 12, 2012

(65) Prior Publication Data
US 2013/0307170 A1 Nov. 21, 2013

Related U.S. Application Data

(60) Provisional application No. 61/358,987, filed on Jun. 28, 2010.

(51) Int. Cl.
| | | |
|---|---|---|
| *A61J 3/07* | (2006.01) | |
| *A61K 9/127* | (2006.01) | |
| *B01J 19/18* | (2006.01) | |
| *A61K 9/00* | (2006.01) | |
| *A61K 38/42* | (2006.01) | |

(52) U.S. Cl.
CPC .............. *A61J 3/07* (2013.01); *A61K 9/0026* (2013.01); *A61K 9/1271* (2013.01); *A61K 38/42* (2013.01); *C12Y 106/99* (2013.01); *C12Y 111/01006* (2013.01); *C12Y 115/01001* (2013.01)

(58) Field of Classification Search
CPC ... A61K 9/127; A61K 9/1271; A61K 9/1277; A61K 38/42; B82Y 5/00; C12Y 115/01001; C12Y 111/01006; B01J 13/02; Y10S 977/773; A23K 1/164; A23L 1/0029; A23L 1/3006; A23L 1/3008; A61J 3/07
USPC ......... 428/402–402.24, 403, 404, 407, 321.1, 428/474.4; 427/331, 389.9, 212, 427/213–213.36, 483, 256; 264/534, 5, 41, 264/4–4.7; 424/400, 408, 450, 451, 455, 424/93.7, 184.1, 497, 489, 501, 490, 491, 4, 424/92, 493, 494, 495
See application file for complete search history.

(56) References Cited

U.S. PATENT DOCUMENTS

| | | | |
|---|---|---|---|
| 4,789,633 A | 12/1988 | Huang et al. | |
| 4,925,661 A | 5/1990 | Huang | |
| 4,983,397 A | 1/1991 | Schroit et al. | |
| 5,534,241 A | 7/1996 | Torchilin et al. | |
| 5,648,478 A | 7/1997 | Henderson | |
| 5,756,069 A | 5/1998 | Torchilin et al. | |
| 5,834,012 A | 11/1998 | Perez-Soler et al. | |
| 6,057,299 A | 5/2000 | Henderson | |
| 6,153,596 A | 11/2000 | Liotta et al. | |
| 6,387,397 B1 | 5/2002 | Chen et al. | |
| 6,476,068 B1 | 11/2002 | Lauria et al. | |
| 6,627,218 B2 | 9/2003 | Huang et al. | |
| 6,723,338 B1 | 4/2004 | Sarris et al. | |
| 6,967,020 B2 | 11/2005 | Tsuchida et al. | |
| 7,951,402 B2 | 5/2011 | Lanphere et al. | |
| 2001/0033860 A1 | 10/2001 | Gwathmey | |
| 2003/0072794 A1 | 4/2003 | Boulikas | |
| 2003/0082228 A1 | 5/2003 | Flowers et al. | |
| 2003/0157158 A1* | 8/2003 | McCully | 424/450 |
| 2003/0203865 A1 | 10/2003 | Harvie et al. | |
| 2003/0212031 A1 | 11/2003 | Huang et al. | |
| 2003/0224037 A1 | 12/2003 | Eriguchi et al. | |
| 2004/0022842 A1 | 2/2004 | Eriguchi et al. | |
| 2004/0071768 A1 | 4/2004 | Sarris et al. | |
| 2004/0142025 A1 | 7/2004 | MacLachlan et al. | |
| 2006/0088583 A1 | 4/2006 | Takeoka et al. | |
| 2007/0003607 A1* | 1/2007 | Awasthi et al. | 424/450 |

FOREIGN PATENT DOCUMENTS

| | | |
|---|---|---|
| CA | 2375854 A1 | 12/2000 |
| WO | 9613250 A1 | 5/1996 |
| WO | 9833481 A1 | 8/1998 |

OTHER PUBLICATIONS

Chang, T.M.S., et al. "Two future generations of blood substitutes based on polyhemoglobin—SOD—catalase and nanoencapsulation," Advanced Drug Delivery Reviews 40:213-218 (2000).
Allen et al., "Advantages of Liposomal Delivery Systems for Anthracyclines", Semin. Oncol. 31(Suppl 13):5-15 (2004).
Papahadjopoulos et al., "Sterically stabilized liposomes: Improvements in pharmacokinetics and antitumor therapeutic efficacy", Proc. Natl. Acad. Sci. U.S.A. 88:11460-11464 (1991).
Weissig et al., "Accumulation of Protein-Loaded Long-Circulating Micelles and Liposomes in Subcutaneous Lewis Lung Carcinoma in Mice", Pharm. Res. 15(10):1552-1556 (1998).

* cited by examiner

*Primary Examiner* — Bijan Ahvazi
*Assistant Examiner* — S. Camilla Pourbohloul
(74) *Attorney, Agent, or Firm* — Nixon Peabody LLP

(57) ABSTRACT

The invention relates to blood substitute compositions, and methods of use thereof. Described herein are compositions in which hemoglobin is maintained substantially in the reduced form of hemoglobin as opposed to the oxidized methemoglobin form through inclusion of an oxido-reductase enzyme and reducing agent within a vesicle with the hemoglobin. The vesicles additionally can comprise a dismutase, a catalase, and an electron acceptor, each of which contribute to either the maintenance of hemoglobin in the active oxygen carrying state or provide a benefit not achieved with free hemoglobin.

11 Claims, 5 Drawing Sheets

1A 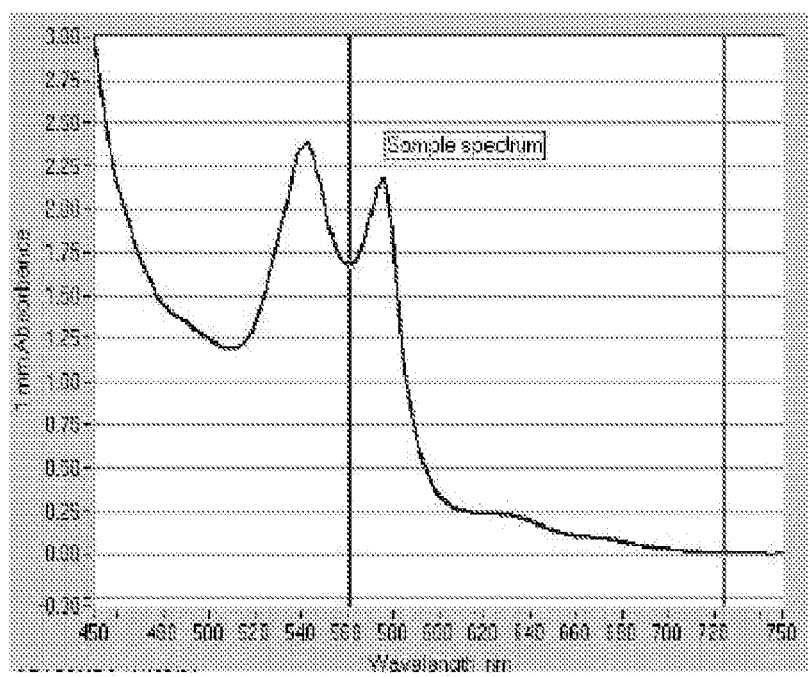
1B 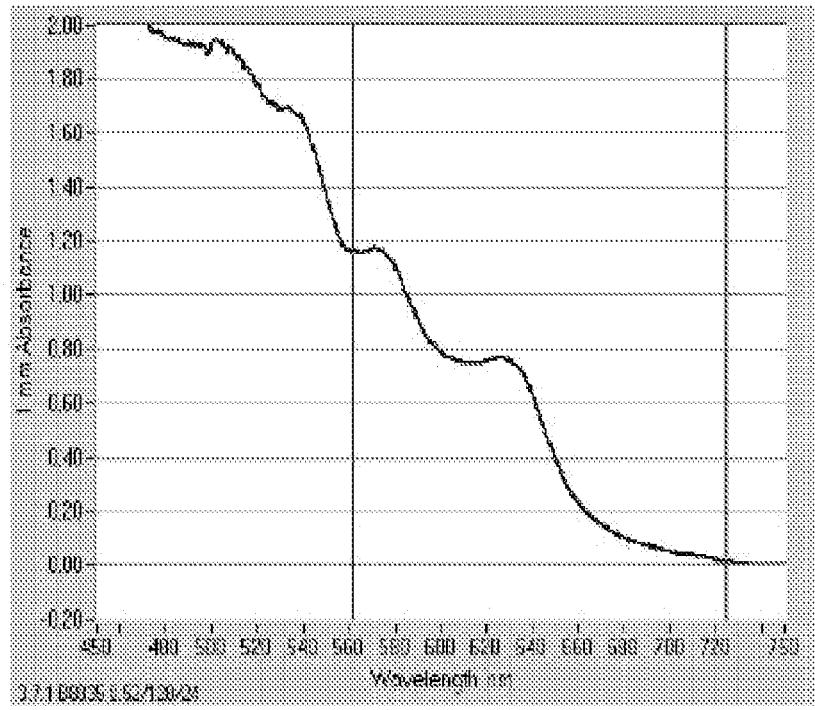
Figures 1A-1H

1C
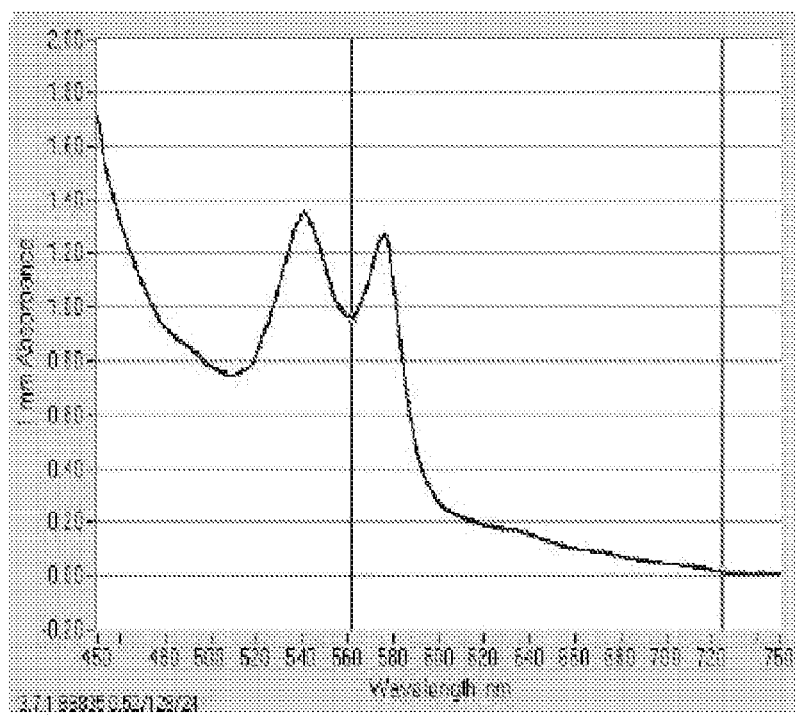
1D
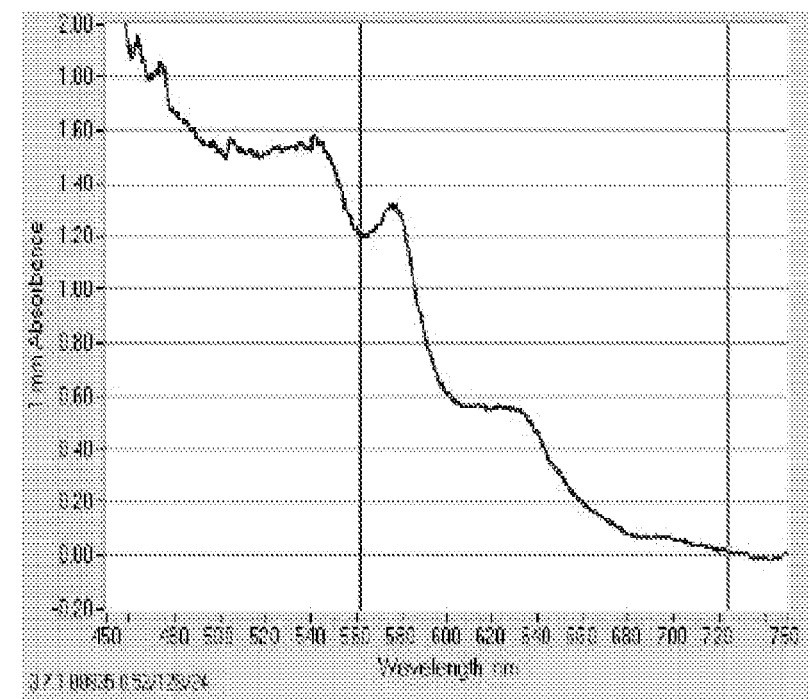
Figures 1A-1H (cont.)

1E
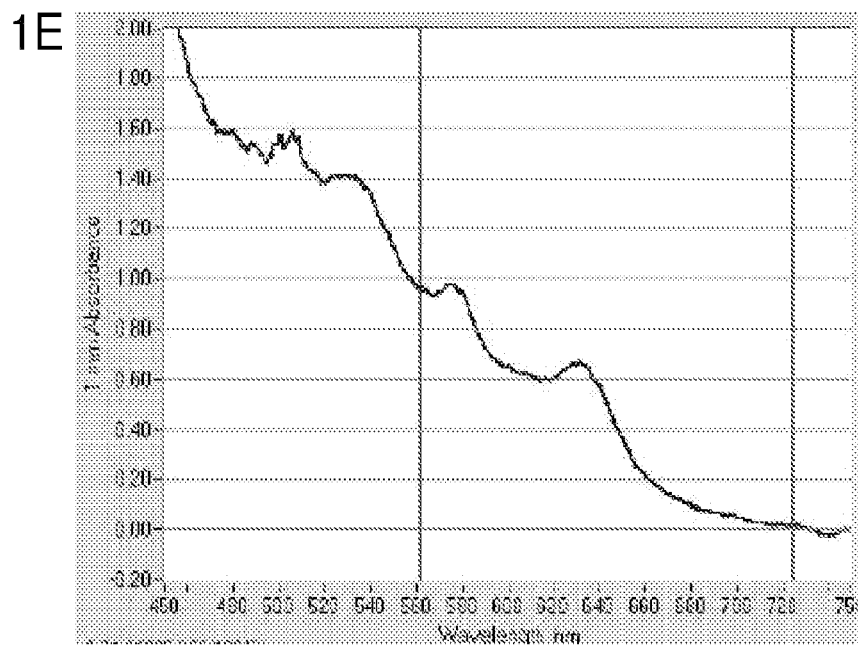
1F
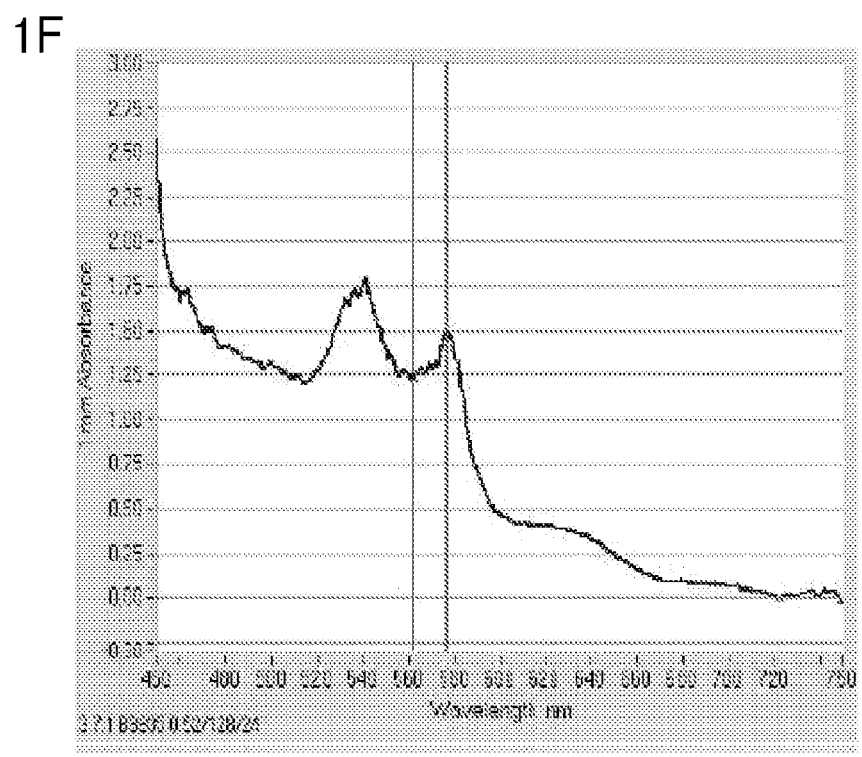
Figures 1A-1H (cont.)

1G
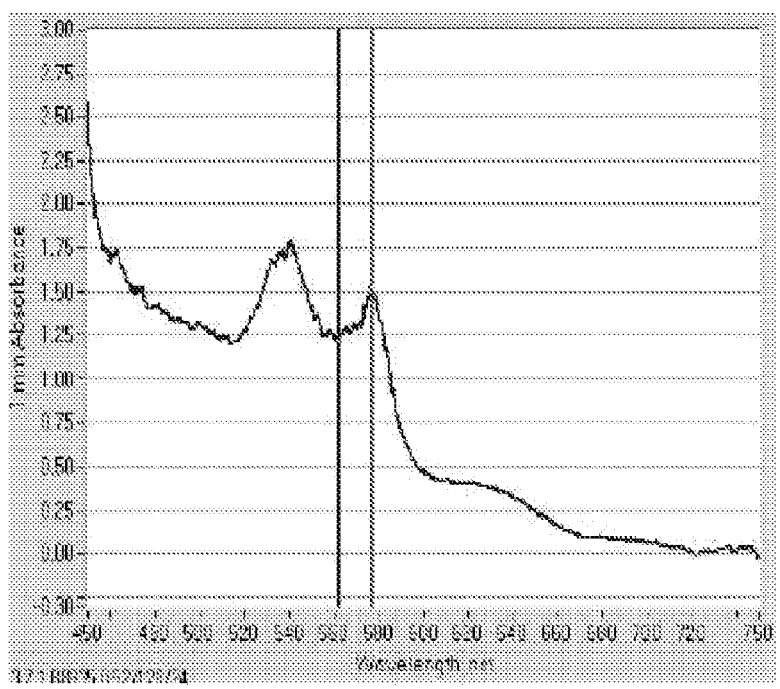
1H
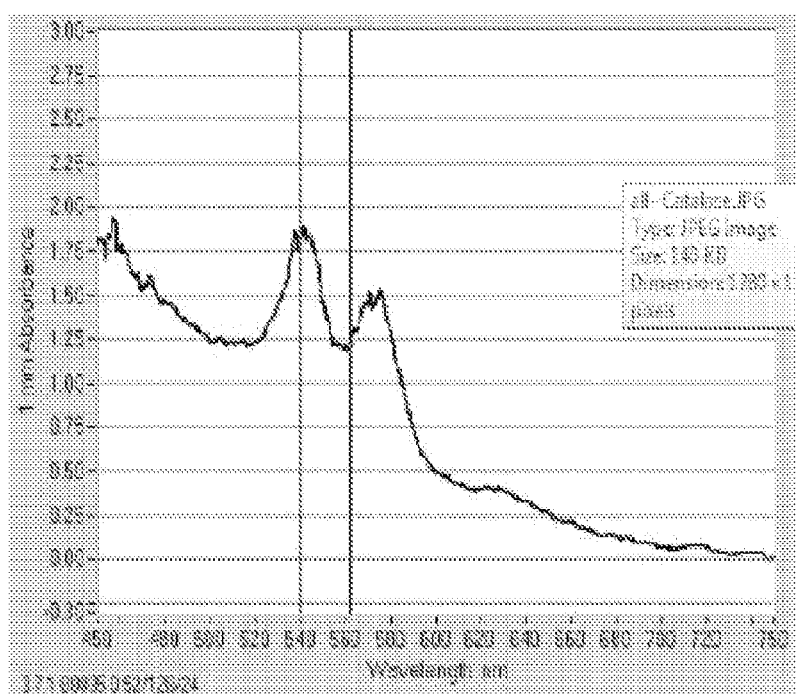
Figures 1A-1H (cont.)

BLOOD SUBSTITUTES AND USES THEREOF

CROSS REFERENCE TO RELATED APPLICATIONS

This application is a 35 U.S.C. 371 National Stage Application of International Application No. PCT/US2011/042213 filed on Jun. 28, 2011, which designates the United States, and which claims the benefit under 35 U.S.C. §119(e) of U.S. Provisional Patent Application Ser. No. 61/358,987, filed Jun. 28, 2010, the contents of which are herein incorporated by reference in their entirety.

GOVERNMENT SUPPORT

This invention was made with Government support under Grant Nos. EB002503 and DK082138 awarded by the National Institutes of Health. The Government has certain rights in this invention.

FIELD OF THE INVENTION

The invention relates to blood substitutes and uses thereof.

BACKGROUND OF INVENTION

The well known complications of blood transfusion, namely incompatibility reactions, disease transmission, immunosuppression and the storage limitations of erythrocytes points to the need for the development of blood substitutes devoid of these shortcomings. The limited availability of certain antigenic blood types and the scarcity of blood products in certain facilities, such as field hospitals also indicate a need for a blood substitute with a more dependable supply chain. Blood substitutes will have numerous applications provided they are safe, meet the viscosity and flow requirements, have the necessary in vivo and shelf life and are cost effective.

It is well known that the hemoglobin molecule is present in erythrocytes and acts as the agent for the transport of oxygen in mammalian circulatory systems by binding and releasing oxygen. Hemoglobin is a conjugated protein with an approximate molecular weight of 64,000. It contains basic proteins, the globins and ferroprotoporphyrin or heme. It is essentially a tetramer consisting of two alpha chains, each containing 141 amino acids, and two beta chains, each containing 146 amino acids. The binding site for oxygen in each of the monomers which make up the tetramer is the Fe(II) molecule in the heme molecule.

Various properties of hemoglobin have been investigated for use in blood substitute products. The four primary issues with Hemoglobin-Based Oxygen Carriers (HBOCs) are the disassociation of the hemoglobin tetramer, the production of free oxygen radicals, the scavenging of nitric oxide, and finally the inactivation of hemoglobin into methemoglobin. While solutions to the first three problems have been proposed, the last problem has not been adequately addressed to permit the use of HBOCs as a viable tool in blood substitution.

SUMMARY OF THE INVENTION

The invention relates to blood substitutes, its compositions, and methods of use. Described herein are compositions in which hemoglobin is maintained substantially in the reduced form of hemoglobin as opposed to the oxidized methemoglobin form through inclusion of an oxido-reductase enzyme and reducing agent within a vesicle with the hemoglobin. The vesicles can additionally comprise a dismutase, a catalase, and an electron acceptor, each of which contribute to either the maintenance of hemoglobin in the active oxygen carrying state or provide a benefit not achieved with free hemoglobin.

In one aspect, the invention provides a lipid vesicle comprising hemoglobin, an oxido-reductase enzyme, a dismutase, a catalase, a reducing agent, and an electron acceptor.

In some embodiments of this and other aspects of the invention described herein, methemoglobin comprises 10% or less of the hemoglobin present in the compositions and formulations described herein.

In some embodiments of this and other aspects of the invention described herein, the oxido-reductase enzyme is DT-diaphorase.

In some embodiments of this and other aspects of the invention described herein the dismutase is a superoxide dismutase.

In some embodiments of this and other aspects of the invention described herein the reducing agent is NADH, or NADPH.

In some embodiments of this and other aspects of the invention described herein the electron acceptor is methylene blue.

In some embodiments, the lipid vesicle further comprises a physiological saline solution. In some embodiments, the physiological saline solution is PBS.

In some embodiments of this and other aspects of the invention described herein, the hemoglobin concentration within the vesicle is 5-15 g/dL, inclusive. In some embodiments, the hemoglobin concentration within the vesicle is comprised between 6.5-10 g/dL, inclusive. In some embodiments, the hemoglobin concentration within the vesicle is comprised between 6.5-8 g/dL, inclusive. In some embodiments, the hemoglobin concentration within the vesicle is comprised between 7.0-7.9 g/dL, inclusive. In some embodiments, the hemoglobin concentration within the vesicle is comprised between 7.25-7.75, g/dL inclusive. In some embodiments, the hemoglobin concentration within the vesicle is 7.5 g/dL.

In some embodiments of this and other aspects of the invention described herein the vesicle size is comprised between 150 nm to 500 nm, inclusive. In some embodiments, the vesicle size is comprised between 180 nm to 220 nm, inclusive. In some embodiments, the vesicle size is 200 nm.

In some embodiments of this and other aspects of the invention described herein the lipid preparation comprises at least one lipid selected from the group consisting of: DPPC, DSPC, DOPC, DLPC, DPPG, DSPG, DHPG, DOPG, DSPEG PEG 5000, DSPE-PEG200, and DOPE-PEG5000.

In some embodiments of this and other aspects of the invention described herein the lipid preparation comprises at least one lipid selected from the group consisting of: DPPC, DSPC, DOPC, and DLPC; at least one lipid selected from the group consisting of: DPPG, DSPG, DHPG, and DOPG; and at least one lipid selected from the group consisting of: DSPEG PEG 5000, DSPE-PEG200, and DOPE-PEG5000.

In some embodiments of this and other aspects of the invention described herein, the lipid vesicles comprise: Cholesterol, DPPC, DSPE-PEG5000, and DPPG. In some embodiments, the ratio of Cholesterol, DPPC, DSPE-PEG5000, and DPPG is respectively 5:5:0.0333:1.

In another aspect, the lipid vesicles described herein are suspended in a physiological saline solution. In some embodiments, the physiological saline solution is PBS. In some embodiments, the concentration of vesicles in the suspension is comprised between $10^{15}$ to $10^{17}$ vesicles/ml inclusive. The saline can further comprise a reducing agent as described herein.

In another aspect, the invention provides a method of encapsulating a blood substitute composition, the method comprising the steps of:
a. mixing a lipid preparation with a composition comprising an oxido-reductase enzyme, a dismutase, a catalase, a reducing agent, and an electron acceptor;
b. extruding the mixture to form lipid vesicles; and
c. isolating lipid vesicles.

In one aspect, described herein is a method of reducing methemoglobin to hemoglobin, the method comprising: contacting, within a lipid vesicle, methemoglobin with a composition comprising: an oxido-reductase enzyme, a dismutase, a catalase, a reducing agent, and an electron acceptor.

In some embodiments, the vesicle is in vitro. In some embodiments, the vesicle is in vivo.

In one aspect, the invention provides a kit. In some embodiments, the kit comprises a first container comprising: hemoglobin, an oxido-reductase enzyme, a dismutase, a catalase, a reducing agent, and an electron acceptor; and a second container comprising a lipid preparation.

In some embodiments, the kit comprises a first container comprising lipid vesicles comprising hemoglobin, an oxido-reductase enzyme, a dismutase, a catalase, and an electron acceptor; a second container comprising a reducing agent, and a physiologically acceptable saline preparation.

In some embodiments, the kit comprises first container comprising lipid vesicles comprising hemoglobin, an oxido-reductase enzyme, a dismutase, a catalase, and an electron acceptor; a second container comprising a reducing agent; and a third container comprising a physiologically acceptable saline preparation.

In some embodiments, the physiologically acceptable saline preparation is phosphate buffered saline (PBS).

DEFINITIONS

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages can mean±1%.

The singular terms "a", "an" and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the term "hemoglobin" refers to the iron-containing oxygen-transport metalloprotein in the red blood cells of all vertebrates. Hemoglobin used in the present invention can be obtained from a variety of mammalian sources, such as, for example, human, or bovine (genus *bos*), or bison (genus *bison*), or ovine (genus *ovis*), or porcine (genus *sus*) sources, or other vertebrates or as transgenically-produced hemoglobin. Alternatively, the hemoglobin for use in the methods and compositions described herein can be synthetically produced by a bacterial cell, or more preferably, by a yeast cell, mammalian cell, or insect cell expression system (Hoffman, S. J. et al., U.S. Pat. No. 5,028,588 and Hoffman, et al., WO 90/13645, both herein incorporated by reference). Alternatively, hemoglobin can be obtained from transgenic animals; such animals can be engineered to express non-endogenous hemoglobin (Logan, J. S. et al. PCT Application No. PCT/US92/05000; Townes, T. M. et al., PCT Application No. PCT/US/09624, both herein incorporated by reference in their entirety). In some embodiments, the hemoglobin for use in the methods and compositions described herein is stroma-free.

As used herein, a "hemoglobin preparation" is a preparation or admixture of either lyophilized or solubilized forms of hemoglobin, oxido-reductase, dismutase, catalase, electron acceptor and reducing agent, each as described herein, in amount and proportion necessary to substantially maintain the hemoglobin in the reduced form, rather than methemoglobin form, for substantially longer than hemoglobin alone. By "substantially longer" in this context is meant at least 5 times longer, preferably at least 6, 7, 8, 9, or 10 times longer or more. By "substantially maintain the hemoglobin in the reduced form" is meant that at least 50% of the hemoglobin is in the reduced form, preferably at least 60%, at least 70%, at least 80% or at least 90% of the hemoglobin is in the reduced form.

As used herein, the term "oxido-reductase enzyme" or "hemoglobin reducing enzyme" refers to a enzyme capable of reducing methemoglobin to hemoglobin.

As used herein, the term "dismutase" refers to an agent which promotes the dismutation of oxygen radicals. A oxygen radical dismutation agent can be an agent that promotes the dismutation of superoxide to oxygen and hydrogen peroxide. A dismutase can be an enzyme.

As used herein "DT-diaphorase" (DTD) refers to a cytosolic flavoenzyme also known as NAD(P)H dehydrogenase, quinone 1 (NQO1), azoreductase, diaphorase-4, dioxin-inducible 1, menadione reductase, quinine reductase 1 (QR1), phylloquinone reductase, and menadione reductase (EC 1.6.99.2). DT-diaphorase is a flavoenzyme capable of utilizing either NADH of NADPH as reducing cofactors to catalyze the direct two-electron reduction of quinones to hydroquinones. DT-diaphorase can act as an antioxidant, quenching free radicals that are generated by quinone cycling during mitochondrial electron transport.

As used herein, the term "superoxide dismutase" or "SOD" refers to an enzyme that catalyzes the dismutation of superoxide into oxygen and hydrogen peroxide. A superoxide dismutase can be a Cu/Zn superoxide dismutase (which binds both copper and zinc), a Fe or Mn superoxide dismutase (which binds either iron or manganese), or a Ni type superoxide dismutase, (which binds nickel). In humans, three forms of superoxide dismutase are present. SOD1 is located in the cytoplasm, SOD2 in the mitochondria and SOD3 is extracellular. The first is a dimer (consists of two units), while the others are tetramers (four subunits). SOD1 and SOD3 contain copper and zinc, while SOD2 has manganese in its reactive centre. The genes are located on chromosomes 21, 6 and 4, respectively (21q22.1, 6q25.3 and 4p15. 3-p15.1).

As used herein, the term "electron acceptor" refers to a chemical entity that has a tendency to attract an electron from another chemical entity, while the term "electron donor" refers to a chemical entity that has a tendency to provide an electron to another chemical entity. In some instances, an electron acceptor can have a tendency to attract an electron from an electron donor. It should be recognized that electron attracting and electron providing characteristics of a chemical entity are relative. In particular, a chemical entity that serves as an electron acceptor in one instance can serve as an electron donor in another instance. Examples of electron acceptors include positively charged chemical entities and chemical entities including atoms with relatively high electronegativities. Examples of electron donors include negatively charged chemical entities and chemical entities including atoms with relatively low electronegativities. Examples of electron acceptors include but are not limited to: methylene blue, sodium 2,6-dibromophenol-indophenol, sodium 2,6-dichlorophenol-indophenol, sodium o-cresol indophenols, indigotetrasulfonic acid, indigotrisulfonic acid, indigo carmine, indigomono sulfonic acid, phenosafranin, safranin T, neutral red, and thionine (i.e. Lauth's violet).

As used herein, the term "catalase" refers to an enzyme capable of catalyzing a reaction which decomposes peroxide (EC1.11.1.6). Catalase can be derived from human, bovine, rodent or other mammalian sources, bacteria, yeast, plants, flowers, and roots.

As used herein, the term "methylene blue" is intended to mean 3,7-bis(dimethylamino)phenazathionium chloride, and its pharmaceutically acceptable salts. Methylene blue acts as an alternative electron acceptor. Methylene blue provides an artificial electron acceptor for NADPH methemoglobin reductase and can serve as an artificial electron acceptor for oxido-reductases as described herein including, but not limited to, DT-diaphorase.

As used herein, the term "reducing agent" refers the element or compound in a reduction-oxidation reaction that donates an electron to another element or compound. Reducing agents include but are not limited to NADH, and NADPH, FADH2, glutathione, cysteine, and L-ascorbic acid.

As used herein, "physiological saline solution" is one in which the salt concentration is substantially the same as that of mammalian tissues, generally about 0.9% w/v. The term includes, but is not limited to, phosphate buffered saline "PBS". A physiological saline solution can include salt/buffer preparation to which water can be added to prepare the saline solution for administration.

As used herein, "PBS" refers to phosphate buffered saline solutions. Some PBS formulations do not contain potassium, while others contain calcium or magnesium.

As used herein, "lipid vesicle" or "liposome" refers to vesicles surrounded by a bilayer formed of lipid components usually including lipids optionally in combination with non-lipidic components. The interior of a vesicle is generally aqueous.

As used herein, a "subject" means a human or animal. Usually the animal is a vertebrate such as a primate, rodent, domestic animal or game animal. Preferably, the subject is a mammal. The mammal can be a human, non-human primate, mouse, rat, dog, cat, horse, or cow, but are not limited to these examples. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

BRIEF DESCRIPTION OF THE DRAWINGS

FIGS. 1A-1H show the spectra of the forms of hemoglobin present in certain compositions, indicating their stability. FIG. 1A shows the spectra of oxyhemoglobin. FIG. 1B shows the spectra of methemoglobin. FIG. 1C shows the spectra of a composition comprising NADH, methylene blue, superoxide dismutase, and catalase. FIG. 1D shows the spectra of a composition comprising NADH, DT-Diaphorase, superoxide dismutase, and catalase. FIG. 1E shows the spectra of a composition comprising DT-Diaphorase, methylene blue, superoxide dismutase, and catalase. FIG. 1F shows the spectra of a composition comprising NADH, DT-Diaphorase, and methylene blue. 1G shows the spectra of a composition comprising NADH, DT-Diaphorase, methylene blue and catalase. 1H shows the spectra of a composition comprising NADH, DT-Diaphorase, methylene blue and superoxide dismutase.

DETAILED DESCRIPTION OF THE INVENTION

Blood Substitute

Figure 2:
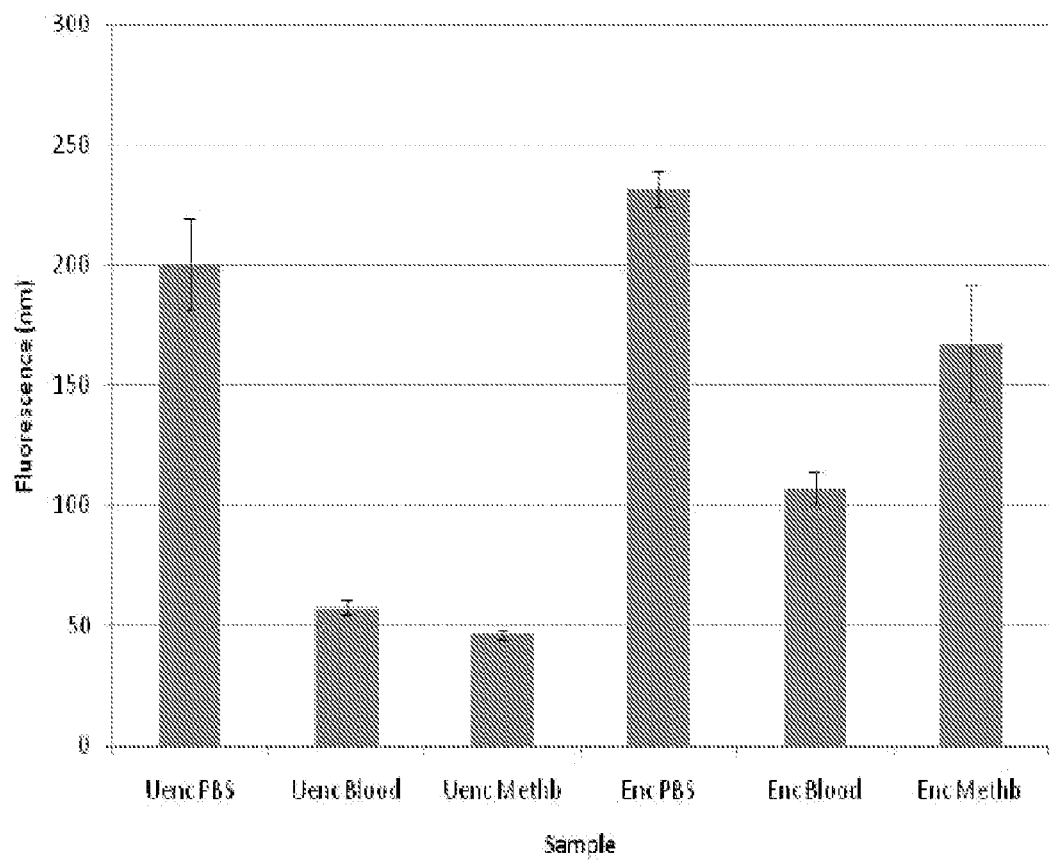
FIG. 2 shows the difference of nitric oxide scavenging between encapsulated hemoglobin-based blood substitute (HBBS) and unencapsulated HBOC.

The properties of hemoglobin present four hurdles to its use in blood substitutes. The first problem, the disassociation of hemoglobin from tetramers into dimers poses a problem because the size of the hemoglobin molecules in their dimeric form means that they are rapidly filtered by the kidneys. Preliminary work by Baxter in the 1970's led to the creation of diaspirin linked hemoglobin which covalently bonded the hemoglobin together into tetramers (Creteur, J., et al., Diaspirin cross-linked hemoglobin improves oxygen extraction capabilities in endotoxic shock. J. Appl Physiol. 2000. 89(4): p. 1437-44). Further, as described herein, maintaining a high local concentration of hemoglobin favors the formation and maintenance of the tetrameric form.

Regarding the second problem, the formation of free oxygen radicals makes the hemoglobin toxic to hepatocytes as well as other metabolically active tissues. Others have proposed methods such as the engineering of the hemoglobin molecule to reduce the affinity of the heme group to oxygen (Winslow, R. M., Cell-free oxygen carriers: scientific foundations, clinical development, and new directions (Biochim Biophys Acta, 2008. 1784(10): p. 1382-6). However, reducing the affinity for oxygen is a less than optimal solution for a molecule to be used to carry oxygen. This issue is addressed herein by inclusion of a dismutase in the blood substitute preparation described.

The third problem, nitric oxide scavenging, appears to lead to vasoconstriction, and appears to be one of the primary reasons for clinical failure of current naked HBOC's (Yu, B., et al., Prevention of the pulmonary vasoconstrictor effects of HBOC-201 in awake lambs by continuously breathing nitric oxide. Anesthesiology, 2009. 110(1): p. 113-22). This problem is addressed in the compositions and methods described herein, by the encapsulation of hemoglobin within a lipid vesicle. The presence of a non-polar encapsulation barrier appears to present a barrier to the nitric oxide and thus lowers its binding to hemoglobin.

The fourth and final problem that prevents hemoglobin from being a viable blood substitute is that becomes inactivated by transformation into methemoglobin. Described herein are compositions and methods which provide hemoglobin in the active oxygen-carrying state for use as a blood substitute. As used herein, "blood substitute" refers to a hemoglobin preparation encapsulated in lipid vesicles which are suspended in a physiological acceptable saline solution, as described herein, and ready to be administered to a subject.

Methemoglobin to Hemoglobin Transformation

Both hemoglobin in vivo and isolated hemoglobin (Fe(II)) tend to be spontaneously oxidized to the methemoglobin (Fe(III)) form, which has a sharply reduced capacity to carry oxygen (Yubisui, T., M. Takeshita, and Y. Yoneyama, J Biochem, 1980 87(6):1715-20). The problem with the addition of the extra positive charge is that the heme group in hemoglobin never adopts a planar conformation and therefore cannot bind to oxygen. Given the free energies of the two forms, Fe(III) being −825.50 kJ/mol, and Fe(II) being −549.4 kJ/mol, the activation of methemoglobin appears to be spontaneous, and therefore cannot be prevented from occurring. In vivo, the NADH-dependent enzyme methemoglobin reductase (diaphorase I) is responsible for reducing methemoglobin in which the iron in the heme group is in the $Fe^{3+}$ (ferric) state, back to hemoglobin, which comprises iron in the $Fe^{2+}$ (ferrous) state. Thus, described herein is an active solution, similar to that of a sacrificial anode, to preserve the integrity of the hemoglobin.

In some embodiments, at least 70% of the hemoglobin in the blood substitute composition is in its reduced form. In further embodiments, at least 75% of the hemoglobin in the blood substitute composition is in its reduced form, alternatively, at least 80%, 85%, 90%, 95% or more, e.g., at least 97.5%, 98%, 99% or more of the hemoglobin is in the reduced form.

In some embodiments, the blood substitute composition comprises no more than 30% methemoglobin. In some embodiments, the blood substitute composition comprises no more than 25% methemoglobin. In some embodiments, the blood substitute composition comprises no more than 20% methemoglobin. In some embodiments, the blood substitute composition comprises no more than 15% methemoglobin. In some embodiments, the blood substitute composition comprises no more than 10% methemoglobin. In some embodiments, the blood substitute composition comprises no more than 5% methemoglobin. In some embodiments, the blood substitute composition comprises no more than 1% methemoglobin.

Compositions

Hemoglobin

In the compositions and methods described herein, "hemoglobin" refers to the iron-containing oxygen-transport metalloprotein in the red blood cells of all vertebrates. Hemoglobin used in the present invention may be obtained from a variety of sources. In some embodiments, the source of hemoglobin can be human. The sequences of genes encoding the human hemoglobin subunits are known to those skilled in the art (hemoglobin beta, NCBI Gene ID No: 3043; hemoglobin gamma, NCBI Gene ID No: 3048; hemoglobin gamma A, NCBI Gene ID No: 3047; hemoglobin alpha 2, NCBI Gene ID No: 3040; hemoglobin delta, NCBI Gene ID No: 3045; and hemoglobin epsilon 1, NCBI Gene ID No: 3046). In some embodiments, the source of hemoglobin can be bovine. In some embodiments, the source of hemoglobin can be, e.g., bison, ovine, or porcine. In some embodiments, the source of hemoglobin can be from other vertebrates. In some embodiments, the hemoglobin can be transgenically-produced hemoglobin. In some embodiments, the hemoglobin can be synthetic. In some embodiments, the hemoglobin can be from transgenic animals. In some embodiments, the source of hemoglobin can be a non-endogenous hemoglobin source. In some embodiments, the source of hemoglobin can be a stroma-free hemoglobin source.

Hemoglobin can be obtained commercially, for example human hemoglobin is available from Sigma-Aldrich as catalog number #H7379 (St. Louis, Mo.).

Free hemoglobin has nitric oxide scavenging ability that limits its utility as a blood substitute. The encapsulation of hemoglobin described herein for maintaining hemoglobin in the reduced, oxygen-carrying tetrameric form has the added benefit of restricting the nitric oxide scavenging activity of the hemoglobin. Thus the nitric oxide scavenging activity is at least 50% lower than that observed with free hemoglobin and preferably at least 60%, at least 70%, at least 80%, at least 90% lower, or more. In a preferred embodiment, the nitric oxide scavenging activity is less than 10% of that observed with free hemoglobin.

Oxido-Reductase Enzyme

In one aspect of the compositions and methods described herein, an oxido-reductase enzyme, along with a reducing agent (see below) permits the overall reduction of the inactive methemoglobin to the active hemoglobin form. In another aspect, to minimize the amount of oxidoreductase used, the composition comprises an electron acceptor (see below), which greatly increases the activity rate of the oxido-reductase.

Oxido-reductase enzymes are classified by the nomenclature of a committee of the International Union of Biochemistry and Molecular Biology (NC-IUBMB; see the World Wide Web at http://chem.qmul.ac.uk/iubmb/enzyme/EC1/). Oxido-reductases classified as, for example, EC1.1 to EC1.22, are contemplated for use in the methods and compositions described herein.

In some embodiments, the source of oxido-reductase can be human. In some embodiments, the source of oxido-reductase can be bovine. In some embodiments, the source of oxido-reductase can be, e.g. bison, ovine, or porcine. In some embodiments, the source of oxido-reductase can be from other vertebrates. In some embodiments, the oxido-reductase can be transgenically-produced oxido-reductase. In some embodiments, the oxido-reductase can be synthetic. In some embodiments, the oxido-reductase can be from transgenic animals. In some embodiments, the source of oxido-reductase can be a non-endogenous oxido-reductase source.

In some embodiments, the oxido-reductase enzyme is DT-diaphorase. DT-Diaphorase is an enzyme, the primary activity of which is to maintain the activity of cytochromes (Gan, Y., et al., Expression of DT-diaphorase and cytochrome P450 reductase correlates with mitomycin C activity in human bladder tumors. *Clin Cancer Res* 2001. 7(5): p. 1313-9). The sequences of genes encoding the human DT-diaphorase are known to those skilled in the art (NCBI Gene ID No:1728). DT-diaphorase is also commercially available. For example recombinant human DT-diaphorase is available from Sigma Aldrich as catalog number D1315 (St. Louis, Mo.).

In some embodiments, the oxido-reductase enzyme is a quinone reductase. In some embodiments, the oxido-reductase enzyme is a NADPH:quinone oxidoreductase. In some embodiments, the oxido-reductase enzyme is a NADPH2:quinone reductase.

In some embodiments, the oxido-reductase enzyme can be, for example, NADH methemoglobin reductase (cytochrome-b5 reductase). In some embodiments, the oxido-reductase enzyme can be, for example, NADPH methemoglobin reductase.

In some embodiments, the oxido-reductase enzyme can be part of, for example an ascorbic acid enzyme system. In some embodiments, the oxido-reductase enzyme can be part of, for example, a glutathione enzyme system.

Dismutases

As used herein, the term "dismutase" refers to an agent which promotes the dismutation of oxygen radicals. A oxygen radical dismutation agent can be an agent that promotes the dismutation of superoxide to oxygen and hydrogen peroxide. A dismutase can be, but is not limited to, superoxide dismutase, melanin, macrocyclic dioxotetraamine, hydrocortisone and nitroxide compounds.

In some embodiments, the source of dismutase can be human. In some embodiments, the source of dismutase can be bovine. In some embodiments, the source of dismutase can be, e.g. bison, ovine, or porcine. In some embodiments, the source of dismutase can be from other vertebrates. In some embodiments, the dismutase can be transgenically-produced dismutase. In some embodiments, the dismutase can be synthetic. In some embodiments, the dismutase can be from transgenic animals. In some embodiments, the source of dismutase can be a non-endogenous dismutase source.

In some embodiments, the dismutase can be superoxide dismutase (SOD). In some embodiments, the SOD can be human. In humans, three forms of superoxide dismutase are present. SOD1 is located in the cytoplasm, SOD2 in the mitochondria and SOD3 is extracellular. The sequences of the genes encoding the human SOD enzymes are known to those skilled in the art (SOD1, NCBI Gene ID No: 6647; SOD2, NCBI Gene ID No: 6648; SOD3, NCBI Gene ID No: 6649). SOD is also available commercially, for example, human SOD is available from Sigma Aldrich as catalog number S9636 (St. Louis, Mo.).

Catalases

In the methods and compositions described herein, catalase (EC1.11.1.6) is used as an enzyme capable of catalyzing a reaction which decomposes hydrogen peroxide to water and oxygen. As used in the methods and compositions described herein, a catalase eliminates or reduces the oxygen radicals formed by hemoglobin.

In some embodiments, the source of catalase can be human. In some embodiments, the source of catalase can be an organism other than human. In some embodiments, the source of catalase can be bovine. In some embodiments, the source of catalase can be, e.g. bison, ovine, or porcine. In some embodiments, the source of catalase can be from other vertebrates. In some embodiments, the source of catalase is from a non-vertebrate. In some embodiments, the source of catalase can be bacterial. In some embodiments, the catalase can be transgenically-produced catalase. In some embodiments, the catalase can be synthetic. In some embodiments, the catalase can be from transgenic animals. In some embodiments, the source of catalase can be a non-endogenous catalase source.

In some embodiments, the catalase can be human. The sequences of the gene encoding the human catalase is known to those skilled in the art (NCBI Gene ID No: 847). Catalase is also available commercially, for example, human catalase is available from Sigma Aldrich as catalog number C3556 (St. Louis, Mo.) and catalase from *Aspergillus niger* is available from Sigma Aldrich as catalog number C3515.

Reducing Agents

As used herein, the term "reducing agent" refers the element or compound in a reduction-oxidation reaction that donates an electron to another element or compound. In some embodiments, the reducing agent comprises NADH. In some embodiments, the reducing agent comprises NADPH. Other reducing agents are potentially of use in the compositions and methods described herein. For example, in some embodiments, the reducing agent comprises FADH2. In some embodiments, the reducing agent is glutathione. In some embodiments, the reducing agent is or comprises cysteine. In some embodiments, the reducing agent is or comprises L-dopa. In some embodiments, the reducing agent comprises L-ascorbic acid. In some embodiments, the reducing agent comprises sodium dithionite. In some embodiments, the reducing agent comprises dithiothreitol. It is preferable that the reducing agent is non-toxic at the concentration used.

In some embodiments, the source of reducing agent can be human. In some embodiments, the source of reducing agent can be an organism other than human. In some embodiments, the source of reducing agent can be bovine. In some embodiments, the source of reducing agent can be, e.g. bison, ovine, or porcine. In some embodiments, the source of reducing agent can be from other vertebrates. In some embodiments, the source of reducing agent is from a non-vertebrate. In some embodiments, the source of reducing agent can be bacterial. In some embodiments, the reducing agent can be transgenically-produced reducing agent. In some embodiments, the reducing agent can be synthetic. In some embodiments, the reducing agent can be from transgenic animals. In some embodiments, the source of reducing agent can be a non-endogenous reducing agent source.

Reducing agents are available commercially. For example, NADH is available from Sigma Aldrich (catalog No: N4505; St. Louis, Mo.). NADPH is also available commercially from Sigma Aldrich (catalog No: N5130).

Electron Acceptors

In the methods and compositions described herein, "electron acceptor" refers to a chemical entity that has a tendency to attract an electron from another chemical entity, while the term "electron donor" refers to a chemical entity that has a tendency to provide an electron to another chemical entity. In some instances, an electron acceptor can have a tendency to attract an electron from an electron donor. It should be recognized that electron attracting and electron providing characteristics of a chemical entity are relative. In particular, a chemical entity that serves as an electron acceptor in one instance can serve as an electron donor in another instance. However, within the methods and compositions described herein, what is important is how the electron acceptor behaves in that context. That is, the contemplated electron acceptors useful in the methods and compositions described herein will, in fact, serve as electron acceptors in the subject methods and compositions. In some embodiments, electron acceptors include positively charged chemical entities. In some embodiments, electron acceptor include chemical entities including atoms with relatively high electronegativities. In some embodiments, the electron acceptor comprises methylene blue. Other electron acceptors can be used, thus, in some embodiments, the electron acceptor comprises sodium 2,6-dibromophenol-indophenol. In some embodiments, the electron acceptor comprises sodium 2,6-dichlorophenol-indophenol. In some embodiments, the electron acceptor comprises a sodium o-cresol indophenols. In some embodiments, the electron acceptor comprises indigotetrasulfonic acid. In some embodiments, the electron acceptor comprises indigotrisulfonic acid. In some embodiments, the electron acceptor comprises indigo carmine. In some embodiments, the electron acceptor comprises indigomono sulfonic acid. In some embodiments, the electron acceptor comprises phenosafranin.

In some embodiments, the electron acceptor comprises safranin T. In some embodiments, the electron acceptor comprises neutral red. In some embodiments, the electron acceptor comprises thionine. In some embodiments, the electron acceptor comprises Lauth's violet. In some embodiments, the electron acceptor comprises a physiologically acceptable electron acceptor. It is preferred that the electron acceptor is non-toxic at the concentration used.

In some embodiments, the electron acceptor is at a concentration of about 0.1% w/v to about 1% w/v. In some embodiments, the electron acceptor is at a concentration of about 0.2% w/v to about 0.8% w/v. In some embodiments, the electron acceptor is at a concentration of 0.25% w/v to 0.75% w/v inclusive. In some embodiments, the electron acceptor is at concentration of 0.5% w/v.

In some embodiments, methylene blue is at a concentration of about 0.1% w/v to about 1% w/v. In some embodiments, the methylene blue is at a concentration of about 0.2% w/v to about 0.8% w/v. In some embodiments, methylene blue is at a concentration of 0.25% w/v to 0.75% w/v inclusive. In some embodiments, methylene blue is at concentration of 0.5% w/v.

Hemoglobin Preparation

A "hemoglobin preparation" or "methemoglobin reducing system" comprises a preparation or admixture of either lyophilized or solubilized forms of hemoglobin, oxidoreductase, dismutase, catalase, electron acceptor and reducing agent, each as described herein, in amount and proportion necessary to substantially maintain the hemoglobin in the reduced form, rather than methemoglobin form, for substantially longer than hemoglobin alone. In particular embodiments, the hemoglobin preparation does not comprise a reducing agent at the time it is encapsulated in the lipid vesicles; in these situations, a reducing agent is added to the physiologically acceptable saline solution as described herein (see below). In these situations, the reducing agent can be present in the physiologically acceptable saline solution at a substantially higher concentration than is desired for it to be present within the lipid vesicles. This approach will ensure migration of the reducing agent into the lipid vesicles at a useful concentration. The reducing agent must be present at the time of administration to a subject as it is required in order for the methemoglobin reducing system to function.

Particles

The compositions of this disclosure are useful for carrying and delivery of oxygen, and have the form of oxyhemoglobin in particulate lipid vesicles or liposomes. These forms can include nanoparticles of various diameters.

Liposomes/Lipid Vesicles

One major type of liposomal composition not generally found in nature includes phospholipids other than naturally-derived phosphatidylcholine. Neutral lipid vesicle compositions, for example, can be formed from dimyristoyl phosphatidylcholine (DMPC) or dipalmitoyl phosphatidylcholine (DPPC). Anionic lipid vesicle compositions generally are formed from dimyristoyl phosphatidylglycerol. Another type of liposomal composition is formed from phosphatidylcholine (PC) such as, for example, soybean PC, and egg PC. Another type is formed from mixtures of phospholipid and/or phosphatidylcholine and/or cholesterol. Lipids for lipid vesicle or liposome formation are known in the art or described herein below.

Liposomes are formed by the self-assembly of phospholipid molecules in an aqueous environment. The amphipathic phospholipid molecules form a closed bilayer sphere in an attempt to shield their hydrophilic groups from the aqueous environment, while still maintaining contact with the aqueous phase via the hydrophilic head group. The resulting closed sphere can encapsulate aqueous soluble drugs or agents such as the hemoglobin, enzyme and cofactor compositions described herein, within the bilayer membrane.

Non-limiting examples of liposome compositions include those described U.S. Pat. Nos. 4,983,397; 6,476,068; 5,834,012; 5,756,069; 6,387,397; 5,534,241; 4,789,633; 4,925,661; 6,153,596; 6,057,299; 5,648,478; 6,723,338; 6,627218; U.S. Pat. App. Publication Nos: 2003/0224037; 2004/0022842; 2001/0033860; 2003/0072794; 2003/0082228; 2003/0212031; 2003/0203865; 2004/0142025; 2004/0071768; International Patent Applications WO 00/74646; WO 96/13250; WO 98/33481; Papahadjopolulos D, Allen T M, Gbizon A, et al. "Sterically stabilized liposomes. Improvements in pharmacokinetics and antitumor therapeutic efficacy" Proc Natl Acad Sci U.S.A. (1991) 88: 11460-11464; Allen T M, Martin F J. "Advantages of liposomal delivery systems for anthracyclines" Semin Oncol (2004) 31: 5-15 (suppl 13). Weissig et al. Pharm. Res. (1998) 15: 1552-1556 each of which is incorporated herein by reference in its entirety.

In some embodiments, the lipid vesicle comprises at least one lipid chosen from one or more, two or more, three or more, or each of the following groups:

Group a. Cholesterol

Group b. DPPC (1,2-dipalmitoyl-sn-glycero-3-phosphocholine); DSPC: 1,2-distearoyl-sn-glycero-3-phosphocholine; DOPC: 1,2-dioleoyl-sn-glycero-3-phosphocholine; and/or DLPC: 1,2-dilauroyl-sn-glycero-3-phosphocholine.

Group c. DPPG: 1,2-dipalmitoyl-sn-glycero-3-[phospho-rac-(3-lysyl(1-glycerol))] (chloride salt); DSPG: 1,2-distearoyl-sn-glycero-3-phospho-(1'-rac-glycerol); DHPG: 3,5-Dihydroxyphenylglycine; and/or DOPG: 1,2-dioleoyl-sn-glycero-3-[phospho-rac-(3-lysyl(1-glycerol))].

Group d. DOPE-PEG5000 (1,2-dioleoyl-sn-glycero-3-phosphoethanolamine); DSPE-PEG200 (1,2-distearoyl-sn-glycero-3-phosphoethanolamine-N-[maleimide(polyethylene glycol)-2000]) and/or DSPEG PEG 5000: (1,2-distearoyl-sn-glycero-3-phosphoethanolamine-N-[folate(polyethylene glycol)-5000] (ammonium salt)).

In some embodiments, the proportion of Group (d) lipids (i.e. lipids containing PEG) is not greater than 1 part in 11.0333 parts. In some embodiments, one or more lipid from Group (d) is present in less that 0.03% by weight. In some embodiments, one or more lipid from Group (d) is present in 0.005%-0.03% by weight. In some embodiments, one or more lipid from Group (d) is present in 0.015%-0.0296% by weight. In some embodiments, one or more lipid from Group (d) is present in 0.029534% by weight. In some embodiments, cholesterol is present in 0.1-0.0.5% by weight. In some embodiments, cholesterol is present in 0.15-0.0.35% by weight. In some embodiments, cholesterol is present in 0.25-0.0.45% by weight. In some embodiments, cholesterol is present in 0.2955373% by weight. In some embodiments, one or more lipid from Group (b) is present in 0.1%-1% by weight. In some embodiments, one or more lipid from Group (b) is present in 0.25%-0.75% by weight. In some embodiments, one or more lipid from Group (b) is present in 0.5610509% by weight. In some embodiments, one or more lipid from Group (c) is present in 0.01%-0.5% by weight. In some embodiments, one or more lipid from Group (c) is present in 0.05%-0.2% by weight. In some embodiments, one or more lipid from Group (c) is present in 0.1138784% by weight. In some embodiments, the ratio of Cholesterol, Group (b) lipids, Group (c) lipids, and Group (d) lipid is 5:5:0.0333:1. In some embodiments, Cholesterol is present in 0.2955373% by weight, Group (b) lipids are present in 0.5610509% by weight, Group (c) lipids are present in 0.1138784% by weight, and Group (d) lipids are present in 0.0295334% by weight.

In some embodiments the vesicles comprise a mixture of two or more individual lipids. In some embodiments, in a mixture of lipids, the lipids have similar phase transition temperatures. In some embodiments, where lipids with a melting temperature below room temperature are used, hydration and extrusion procedures used to prepared lipid vesicles (see below) can be performed at room temperature.

In some embodiments, the lipid vesicle surface is PEG (polyethylene glycol)-adsorbed to prevent vesicle coalescing.

The vesicles can be from 150 nm in diameter to 500 nm in diameter. However, very small vesicles are rapidly cleared by the kidneys and very large vesicles present problems for circulation. In some embodiments, the vesicles are from 150 nm in diameter to 500 nm in diameter, for example, 150-450 nm inclusive, 150-400 nm inclusive, 150-300 nm inclusive, 150-220 nm inclusive, 170-210 nm inclusive, 180-210 nm inclusive, 190-200 nm inclusive, or about 200 nm in diameter.

Lipid vesicles as described herein can be prepared according to methods used in the preparation of conventional lipid vesicles and PEG-lipid vesicles, as disclosed in e.g. EP-0662820. Passive loading of the active ingredients into the lipid vesicles by dissolving the components in the aqueous phase that is then mixed with a lipid preparation can be sufficient to encapsulate the components, but other methods can also be used. A detailed method for vesicle preparation is provided herein below.

Methods of Encapsulation

Encapsulation of the blood substitute composition can be performed as follows. Dissolve lipids in solvent in the appropriate concentrations (10 mg/ml) to make the stock solutions. Make the mixture of lipids at desired ratio with a total concentration of lipids within the range of 2 mg/mL to 25 mg/mL, inclusive. Heat samples (hemoglobin composition and PBS control) at 40° C. for 30 minutes while making the above mixture. Dry mixture of lipids to completely evaporate off solvent. This should leave only a mixture of the lipids in the desired ratios without solvent at the bottom of the flask. Add 2 ml of sample (hemoglobin composition and PBS) to the lipid mixture and vortex for 1 minute. Let this mixture sit in a 40° C. water bath for 1 hour. Use extruder with appropriate membrane 21 times at 40° C. to get vesicles at the appropriate size. Leave overnight at 4° C. Centrifuge the sample through 100 kDa filters at 1500 rpm for 2 hours. Typically the 1 ml of sample remains after the centrifugation. Apply the sample to a sieving agarose gel column. As hemoglobin tends to adhere to the column, first run Phosphate Buffered Saline through. Take samples at 5 drops/well in 96 well plates. The encapsulated sample is the cloudy mixture. Use Dynamic Light Scattering particle sizer to determine which wells contain the desired sample. Pool the wells and store sample at 4° C.

This method can be scaled up by the ordinary skilled artisan.

Carriers

In some embodiments, described herein are pharmaceutical formulations comprising vesicles comprising hemoglobin compositions as described herein and one or more pharmaceutically acceptable carriers, excipients, diluents, stabilizers, preservatives, or other inactive ingredients, including combinations of these, known to skilled artisans and/or described further herein. In some embodiments, the vesicles comprising a hemoglobin composition as described herein are in suspension in a carrier. In some embodiments, the vesicles comprising a blood substitute composition as described herein are present in the carrier at a concentration of $10^{12}$-$10^{18}$ vesicles/mL of carrier. In some embodiments, the vesicles comprising a blood substitute composition as described herein are present in the carrier at a concentration of $10^{15}$-$10^{17}$ vesicles/mL of carrier. In some embodiments, the concentration of vesicles comprising a blood substitute composition as described herein is such that the resulting pharmaceutical composition has an oxygen carrying capacity of 75% to 150% or more, relative to that of normal whole blood. In some embodiments, the concentration of vesicles comprising a hemoglobin composition as described herein is such that the resulting pharmaceutical composition has an oxygen carrying capacity substantially equal to the oxygen carrying capacity of normal whole blood.

Shelf Life

Liposomal dispersions exhibit chemical as well as physical stability characteristics. Chemical stability is related to chemical degradation whereas physical stability relates to the colloidal stability of the system.

The physical stability of liposomal dispersions is determined by the inter-vesicular interactions, which depends on the balance between attractive and repulsive forces. Colloidal systems are stabilized by repulsive forces, i.e. electrostatic repulsion and steric repulsion, due to differences in chemical potential between water in the bulk and in the interaction region.

For the purpose of the present invention "stable liposome compositions" are those in which the dispersed liposomes substantially retain their initial character and show minimal chemical and physical degradation for the desired shelf-life. Liposomes or lipid vesicle stability can be assessed by changes (or lack thereof) in light scattering spectrophotometry measures as known in the art.

"Recommended storage temperature" for a composition is the temperature ($T_s$) at which lipid vesicle is to be stored to maintain its stability over the shelf life of the composition in order to ensure a consistently delivered dose. The recommended storage temperature will vary from about $-70°$ C. to about $40°$ C. In certain embodiments, the recommended storage temperature is between about $-25°$ C. to about $6°$ C. In some embodiments, the recommended storage temperature is about room temperature. Usually a drug product will be kept at a temperature that is at or below the recommended storage temperature.

Without wishing to be bound by theory, biologically compatible molecules such as the lipid vesicles described herein are metabolized easily, and thus they have a relatively short half life in the blood stream. Since the compositions and methods described herein require the blood substitute to remain efficacious for roughly 24 hours, the short half-life is advantageous as the blood substitute is metabolized within a physiologically relevant timeframe. The produced vesicles can be stored at $4°$ C. up to 21 days and at $-20°$ C. for months if lyophilized (Puri, A. et al. Critical reviews in therapeutic drug carrier systems 2009, 26:523).

In Vivo Stability

In some embodiments, the blood substitute compositions provided herein are stable and efficacious in vivo for a number of hours, e.g., for at least 1 hour, for at least 6 hours, for at least 12 hours, for at least 24 hours, or preferably for about 48 hours. The most useful compositions will be stable in vivo (i.e. have an in vivo $T_{1/2}$ of at least 24 hours, preferably at least 30 hours or more, at least 36 hours or more, up to and including at least about 48 hours). In some embodiments, an additional dose of a blood substitute composition as described herein, or another treatment such as a blood transfusion can be administered to the subject within 48 hours of the initial administration of the blood substitute composition as described herein, e.g. within 1 hour of the initial dose, within 6 hours of the initial dose, within 12 hours of the initial dose, within 24 hours of the initial dose, or within 48 hours of the initial dose. In some embodiments, an additional dose of a blood substitute composition as described herein, or another treatment such as a blood transfusion can be administered to the subject when one or more symptoms or indicators of the patient's condition worsens, or ceases improving after the initial administration of the blood substitute composition as described herein, e.g., when the blood or tissue oxygenation levels of the patient cease improving and/or begin to decline.

Methods of Treatment

Pharmaceutical Formulations

In another aspect, described herein are pharmaceutical formulations for treatment of individuals in need thereof, comprising compositions as described herein and one or more pharmaceutically acceptable carriers, excipients, diluents, stabilizers, preservatives, or other inactive ingredients, including combinations of these, known to skilled artisans and described further herein.

In certain embodiments of the pharmaceutical formulations, the hemoglobin composition as described herein is comprised within a lipid vesicle as described herein. In certain embodiments, the formulation comprises the hemoglobin composition within a lipid vesicle, which is suspended in a carrier solution, the carrier solution optionally including NADH/NADPH. In some embodiments, the lipid vesicle comprising the blood substitute should be mixed or suspended in the carrier just prior to administration of the formulation to the subject.

In certain embodiments, the carrier can include one or more of sterile water, a buffer solution or saline, diluent, and combinations thereof. In certain embodiments, the carrier is a phosphate buffered saline. In certain embodiments, the carrier is PBS.

The stability and/or activity of the various enzymes and cofactors of the hemoglobin preparations as described herein can be enhanced or prolonged by choice of the carrier composition. For example, in addition to various physiologically acceptable buffering agents, stabilizing agents such as PEG, albumin, etc. can be included in the hemoglobin preparation encapsulated within the vesicles.

The pharmaceutical formulations can further comprise one or more of different salts, sugars, proteins, starch, gelatin, plant oils, polyethylene glycol and the like, including combinations of two or more of the foregoing.

An additional aspect of the compositions described herein includes use of the compositions and formulations thereof as described herein in the manufacture of a medicament, particularly, the manufacture of a medicament for use in the treatment of conditions requiring blood replacement or substitution as described herein.

Administration

As noted previously, in one aspect there are provided methods of treatment of conditions as described herein using a composition as described herein in a pharmaceutical formulation as described herein.

In one embodiment, the methods may be practiced as a therapeutic approach towards the treatment of the conditions described herein. Thus, in a specific embodiment, the composition or pharmaceutical formulation can be used to treat the conditions described herein in individuals in need thereof, including humans. The methods generally comprise administering to the individual an amount of a composition, or formulation described herein, effective to treat the condition.

In some embodiments, the individual is a mammal, including, but not limited to, human, bovine, horse, feline, canine, rodent, or primate. In other embodiments, the individual is a human. In some embodiments, the methods described herein further comprise selecting a subject in need of treatment.

The terms, "pharmaceutically effective amount" or "therapeutically effective amount" refer to an amount of a composition sufficient to treat a specified disorder, condition or disease or one or more of its symptoms and/or to prevent the occurrence of the disease or disorder. In reference to patients in need of a blood substitute, a pharmaceutically or therapeutically effective amount comprises an amount sufficient to, among other things, cause low blood pressure to return to normal levels and/or to restore normal blood and/or tissue oxygenation levels. In reference to patients in need of a blood substitute, a pharmaceutically or therapeutically effective amount can also comprise an amount sufficient to, among other things, cause blood pressure to fail to decrease further, and/or to cause blood and/or tissue oxygenation levels to fail to decrease further.

When used with respect to methods of treatment and the use of blood substitute compositions, an individual "in need thereof" may be an individual who has been diagnosed with or previously treated for the condition to be treated. With respect to methods of diagnosis and the use of blood substitute compositions, an individual "in need thereof" may be an individual who is suspected to have a condition, is at risk for a condition (e.g. a family history of the condition, life-style factors indicative of risk for the condition (e.g. a patient with ulcers and no *H. pylori* infection is more likely to experience recurrent bleeding of the ulcer) or has previously been diagnosed with the condition (e.g. diagnosis can include monitoring of the severity of the disease over time and/or in conjunction with therapy).

In some embodiments, the condition to be treated is blood loss or insufficient blood levels. Blood loss or insufficient blood levels to be treated by the methods and compositions described herein can be a low level of total blood volume or a low level of a component of blood which causes a reduced oxygenation of the subject's blood and/or tissue or a reduced capability of the subject's blood to provide oxygen throughout their body, e.g. a reduced level of red blood cells.

In some embodiments, blood loss may be due to an injury, amputation, childbirth, major surgery and/or a condition that causes bleeding, e.g., a bleeding ulcer or cancer. In some embodiments, insufficient blood levels can be the result of a disease that destroys blood cells, e.g. hemolytic anemia or thrombocytopenia or a disease that inhibits clotting such that wounds or lesions continue to lose blood beyond a time at which clotting would normally have occurred. In some embodiments, insufficient blood levels can be the result of a disease in which the subject's bone marrow doesn't make enough blood or red blood cells, e.g. aplastic anemia. In some embodiments, a low level of total blood volume and/or a low level of a component of blood can result in ischemia, anemia, and/or hypoxia. In some embodiments, the subject with insufficient blood levels has or is diagnosed as having sickle cell anemia.

The blood substitute compositions, including formulations described herein, can be used alone or in conjunction with (e.g., prior to, concurrently with, or after) other modes of treatment (e.g., clotting factors,). Likewise, the compositions, and formulations thereof, as described herein can be administered before, concurrently, or after the administration of one or more other therapeutic agents. The blood substitute compositions and formulations thereof described herein can also be administered in conjunction with (e.g., prior to, concurrently with, or after) drugs to alleviate the symptoms associated with the condition requiring transfusion of a blood substitute (e.g., ranitidine, antacids, H2 antagonists or prostaglandin analogues to treat ulcers). The blood substitute compositions described herein can also be administered at more than one stage of (including throughout) the treatment of the subject (e.g., after surgery, during surgery, before surgery, etc.).

Other non-limiting examples of therapeutic agents which can be administered before, after or concurrently with the compositions and formulations of the present invention include, antihemorrhagic drugs, either or both hemostatic and/or styptic, such as for example antifininolutics, vitamin K, fibrinogen, and blood coagulation factor, and kaolin; prophylactic antibiotics, acetaminophen, NSAIDs, hydroxyurea (Droxia, Hydrea), chemotherapy, blood transfusion, and platelet transfusion.

Agents for treatment of sickle cell disease include, but are not limited to, prophylactic antibiotics, acetaminophen, NSAIDs and hydroxyurea (Droxia, Hydrea). In certain embodiments, the compositions or formulations described herein can be administered before, during, or after a bone marrow transplantation or administered to a patient in need of a bone marrow transplant.

In certain embodiments, the compositions are administered prior to or after surgery (e.g., to repair trauma, to stop bleeding, etc.). In other embodiments, the compositions are administered after surgery. The optimal combination of one or more treatments such as surgery in conjunction with administration of the compositions described herein, and, optionally, additional one or more therapeutic agents, can be determined by an attending physician based on the individual and taking into consideration the various factors effecting the particular individual, including those described herein.

In conjunction with the methods of use described herein, the blood substitute compositions or pharmaceutical formulations of the present invention can be administered parenterally. Parenteral administration may be accomplished via bolus injection (IV) or via infusion (IV).

Continuous intravenous infusion can be administered over a period of minutes or hours. Times can include, for example, from about 10 minutes to about 5 hours, from about 15 minutes to about 4 hours; from about 30 minutes to about 4 hours; from about 45 minutes to about 4 hours, from about 60 minutes to about 4 hours, from about 45 minutes to about 3 hours, from about 60 minutes to about 2 hours, from about 90 minutes to about 3 hours, from about 90 minutes to about 2 hours. Intravenous infusion can be administered within about 10 minutes, about 15 minutes, about 20 minutes, about 30 minutes, about 45 minutes, about 50 minutes, about 60 minutes, 80 minutes, about 1.5 hours, about 2 hours, about 2.5 hours, about 3 hours, about 3.5 hours, about 4 hours, about 5 hours, about 12 hours, about 24 hours, about 36 hours, or about 48 hours.

Formulation and Dosage

As noted previously, the blood substitute compositions and pharmaceutical formulations as described herein can be administered to individuals in need thereof for the treatment of conditions as described herein in conjunction with the methods of use described herein.

The blood substitute compositions described herein will generally be used in an amount effective to achieve the intended result, for example in an amount effective to treat a deficiency in oxygen carrying capacity and/or volume of blood. The composition can be administered therapeutically to achieve therapeutic benefit. By therapeutic benefit is meant eradication or amelioration of the underlying disorder or deficiency being treated and/or eradication or amelioration of one or more of the symptoms associated with the underlying disorder or deficiency. Therapeutic benefit also includes halting or slowing the progression of the condition, regardless of whether improvement is realized.

In some embodiments, where the condition being treated is blood loss or insufficient blood levels, an effective amount is an amount sufficient to increase and/or restore blood pressure to normal levels (e.g., systolic ≥90 mmHg; diastolic ≥60 mmHg). In some embodiments, where the condition being treated is blood loss or insufficient blood levels, an effective amount is an amount sufficient to increase and/or restore blood and/or tissue oxygenation to normal levels (e.g., a pulse oximeter reading ≥90%).

The amount of compositions administered to achieve a desired therapeutic effect will depend upon a variety of factors, including, for example, the particular condition being treated, the mode of administration, the severity of the condition being treated, the age and weight of the patient, the bioavailability of the composition, the adverse effects experienced by the individual being treated, etc. Determination of an effective dosage is well within the capabilities of those skilled in the art in view of the teachings provided herein.

In certain embodiments, the dose of a composition administered at a particular time point will be in the range from about 5 mL to 2 L or more with a hemoglobin concentration in the vesicles of 5-15 g/dL, inclusive. The volume of a dose of a composition as described herein which is to be administered can vary depending upon factors including, but not limited to, the size and/or age of the subject, the estimated volume of blood lost, the oxygen carrying capacity of the particular composition to be administered, and the subject's response to any prior doses or treatments. Determination of the appropriate dose volume can be performed by one skilled in the art. The formulation administered can have a vesicle concentration of $10^{15}$-$10^{17}$ vesicles/mL, where the hemoglobin concentration in the vesicles is 5-15 g/dL, inclusive.

The dose administered may be higher or lower than the dose ranges described herein, depending upon, among other factors, the bioavailability of the composition, the tolerance of the individual to adverse side effects, the mode of administration and various factors discussed above. Dosage amount and interval may be adjusted individually to provide plasma levels of the composition that are sufficient to maintain therapeutic effect, according to the judgment of the prescribing physician Skilled artisans will be able to optimize effective dosages without undue experimentation in view of the teaching provided herein.

Dosages may also be estimated using in vivo animal models, as will be appreciated by those skill in the art.

Multiple doses (e.g., continuous or bolus) of the compositions as described herein may also be administered to individuals in need thereof over the course of hours, days, weeks, or months. For example, repeat doses can be administered daily, every other day, every 10 days, weekly, monthly, twice weekly, three times a week, twice monthly, three times a month, four times a month, five times a month, every other month, every third month, every fourth month, etc.

Determining Blood Loss

Methods of determining or approximating the blood lost by a patient during a surgery or while under the supervision of a physician are known to those skilled in the art and have been described, for example in U.S. Pat. Nos. 5,236,664; 5,231,032; 3,532,086; and 4,422,548 which are incorporated herein by reference in their entirety. Blood loss is often estimated by medical professionals by observation of pools, puddles, or other visible bodies of blood that has been lost by the subject.

Blood loss can also be estimated, or the need for transfusion determined by observing the subject. Subjects suffering from blood loss or insufficient levels of blood can have an elevated pulse, anemia, cold, clammy and/or pale skin, a decrease in lucidity, combativeness, shallow or rapid breathing, a lowering of the difference in diastolic and systolic blood pressures, a decrease in blood pressure, shock, and/or hypovolemic shock. The severity of blood loss can also be determined by medical professionals by observing the location of the injury or trauma causing the blood loss. Injuries to, for example, the femoral artery, will cause severe blood loss very quickly, while injuries not affecting a major artery or vein will cause less severe blood loss over the same amount of time.

Blood loss equal to or greater than 15% of the subject's total blood volume can indicate a need for transfusion with blood or a blood substitute. Blood loss equal to or greater than 25% of the subject's total blood volume is likely to indicate a need for transfusion with blood or a blood substitute. Regardless of the % of total volume lost, the loss of 1 L of blood in and adult human subject, 0.25 to 0.5 L of blood in a human child, or the loss of 24 mL of blood in a human infant is likely to indicate a need for transfusion with blood or a blood substitute.

Determining Blood Oxygenation

Provided herein are compositions and methods for treating patients having insufficient blood levels which can cause reduced oxygenation of the subject's blood or a reduced capability of the subject's blood to provide oxygen throughout their body, e.g. a reduced level of red blood cells. Such a patient can be identified and/or diagnosed by methods of measuring blood oxygenation known to those skilled in the art.

In some embodiments, blood oxygen saturation can be measured by a pulse oximeter. As well known by those of ordinary skill in the art, a pulse oximeter measures arterial blood oxygen saturation using a sensor arrangement containing two LED's and a photodiode detector. The sensor is applied directly to a well perfused part of a patient, such as at a finger or ear. Each LED of the sensor transmits radiation at a different one of two wavelengths, typically one being red and the other being infrared, to the patient. The photodiode detector is responsive to the red and infrared light for developing red and infrared electrical signals that are affected, via transmission or reflection, by the patient's blood flow in the area between the two LED's and the light receiving portion of the photodiode detector. The greater the oxygenation of the blood, the less of the emitted red light is detected, due to greater absorption of the red light by the patient's blood. In pulse oximeters, the acquired red and infrared signals are processed to develop a measurement indicative of the current blood oxygenation level of the patient. Processing of the red and infrared signals for determining blood oxygenation is based on the Beer-Lambert law, as well known, wherein a ratio is generally used to compare the AC and DC components of the red light ($AC_r$ and $DC_r$ respectively), to the AC and DC components of the infrared light ($AC_{ir}$ and $DC_{ir}$ respectively), in accordance with the following equation:

$$\frac{AC_r/DC_r}{AC_{ir}/DC_{ir}}$$

The resultant value is applied to an experimentally determined reference table to provide the final determination of the measured level of the blood oxygenation. A subject can have insufficient blood levels if their blood oxygen saturation is less than 90% of the experimentally determined normal level, e.g. 90% of the normal level, 85% of the normal level, 80% of the normal level, 70% of the normal level, 50% of the normal level, 20% of the normal level or less.

Additional means of measuring blood oxygenation are known to those skilled in the art and include, but are not limited to, those methods described in U.S. Pat. Nos. 7,400,918; 5,971,930; 7,865,223; 5,924,980; 6,135,958; 7,130,672; 6,298,253; 6,449,501 and U.S. Patent Application Nos: 2004/0064057, 2010/0166252, 2011/376894, 2009/0326352, each of which is incorporated herein by reference in its entirety.

Determining Efficacy

The efficacy of administration of a blood substitute can be determined by the ordinarily skilled clinician. However, a treatment is considered "effective treatment," as the term is used herein, if any one or all of the signs or symptoms of a condition described herein are altered in a beneficial manner, other clinically accepted symptoms are improved, or even ameliorated, e.g., by at least 10% following treatment with a compound as described herein. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human, or a mammal) and includes: (1) inhibiting the disease, e.g., preventing ischemia, hypoxia or crisis episode; or (2) relieving the disease, e.g., causing regression of symptoms. An effective amount for the treatment of a disease means that amount which, when administered to a mammal in need thereof, is sufficient to result in effective treatment as that term is defined herein, for that disease. Efficacy of an agent can be determined by assessing physical indicators, for example as described below. Efficacy can be assessed in animal models of a condition described herein, for example treatment of a mouse following induced blood loss, and any treatment or administration of the compositions or formulations that leads to an increase in blood pressure and/or blood oxygenation or the decrease of at least one symptom, marker, or parameter of a condition described herein.

Efficacy can be measured by a reduction in any of the symptoms of a condition described herein, for example, a reduction in the symptoms of blood loss, e.g. nausea, loss of consciousness, vomiting, rapid breathing, elevated heart rate, low body temperature, and shock. Efficacy can also be measured by a failure of an individual to worsen as assessed by hospitalization or need for medical interventions (i.e., progression of the disease is halted or at least slowed). Efficacy can also be measured by an increase in blood oxygenation levels or a failure of blood oxygenation levels to decrease. Methods of measuring blood oxygenation levels are described herein above. Efficacy can also be measured by an increase in blood pressure or a failure for blood pressure to decrease. Blood pressure can be measured by a sphygmomanometer, palpation, ausculatory methods, oscillometric methods, measurement of arterial blood pressure through an arterial line, arterial pressure measurement with intravascular cannulae, measurement of venous blood pressure and/or pulmonary vessel pressure via a central venous catheter or any other method known to those of skill in the art.

Another marker of the efficacy of treatment as described herein is survival. Statistical survival rates for specific conditions described herein are well established—when an individual or group of individuals treated according to the methods described herein survives beyond the expected time or at a greater than expected rate, the treatment can be considered effective.

The efficacy of treatment according to the methods described herein can be evaluated by following surrogate or indirect markers of blood loss or insufficient blood levels. Other markers that can be determined include, for example, markers of ischemic or hypoxic stress or cell death.

Kits

Also provided are kits for administration of the compositions described herein, including pharmaceutical formulations comprising the compositions.

Given the nature of situations in which blood substitutes are useful, kits containing either blood substitute in an immediately administrable form or components for the preparation of administrable blood substitute have great utility. As such, kits having the following arrangements are described herein: a) a kit comprising one or more unit dosages of blood substitute composition in a delivery container, e.g., an IV bag, and ready for immediate use; b) a kit comprising lipid vesicles as described herein (e.g., a preparation of lipid vesicles comprising hemoglobin, an oxidoreductase, a dismutase, a catalase, an electron acceptor and optionally a reducing agent), and a physiologically acceptable saline solution for suspension of the vesicle preparation prior to administration; c) a kit containing, either separately or in admixture, a dried or solubilized hemoglobin preparation (e.g., a preparation of hemoglobin, oxidoreductase, dismutase, catalase, electron acceptor, and optionally a reducing agent, as necessary to provide a reducing agent for function of the methemoglobin reducing system) and a lipid mixture for the preparation of vesicles containing the hemoglobin preparation. Considerations for kit compositions or arrangements are described further below. A unit dosage is e.g. a unit with an oxygen carrying capacity equal to one unit of whole blood (450 mL).

In certain embodiments the kits may include a unit dosage amount (e.g., as used for therapy) corresponding to the volume and/or oxygen carrying capacity of a unit of whole blood. Of course, kits comprising greater than one unit equivalent of blood substitute can also be advantageous. Formulations comprising 1×, 1.5×, 2×, 2.5× or more oxygen carrying capacity than an equivalent volume of whole blood are specifically contemplated.

Within the context of kits, or for that matter, any other aspect of the methods and compositions described herein, oxygen carrying capacity can be modulated by, for example, increasing the concentration of hemoglobin in the vesicles or by increasing the concentration of vesicles in the administered preparation. It should be understood that increased hemoglobin levels may need to be compensated for by corresponding increases in one or more of the other components (e.g. electron acceptor, oxido-reductase enzyme, catalase, dismutase, reducing agent, etc).

In another aspect of the invention described herein, kits for treating an individual who suffers from or is susceptible to the diseases, disorders or conditions described herein are provided, comprising a first container comprising a unit dosage amount of a hemoglobin preparation or formulations thereof as disclosed herein, and a second container comprising a unit dosage amount of a lipid preparation as described herein.

In certain embodiments, kits for treating an individual who suffers from or is susceptible to the diseases, disorders or conditions described herein are provided, comprising a first container comprising a unit dosage amount of lipid vesicles comprising a hemoglobin preparation or formulations thereof as disclosed herein with the exception of a reducing agent, and a second container comprising a unit dosage amount of a reducing agent and a pharmaceutically acceptable carrier, diluent, adjuvant, etc. for preparation of the composition to be administered to the individual.

In certain embodiments, kits for treating an individual who suffers from or is susceptible to the diseases, disorders or conditions described herein are provided, comprising a first container comprising a unit dosage amount of lipid vesicles comprising a hemoglobin preparation or formulations thereof as disclosed herein with the exception of a reducing agent, and a second container comprising a unit dosage amount of a reducing agent and a third container comprising a pharmaceutically acceptable carrier, diluent, adjuvant, etc. for preparation of the composition to be administered to the individual.

The container may be any of those known in the art and appropriate for storage and delivery of intravenous formulations.

In some embodiments the kits may include a dosage amount (e.g., as used for therapy) of a lipid composition for the preparation of lipid vesicles or a pharmaceutical formulation thereof, as disclosed herein. Additionally, in certain embodiments, the kit can contain a separate dosage amount of a hemoglobin preparation or composition as described herein to be incorporated into vesicles made with the lipid preparations described herein.

Additionally, kits described herein can provide the composition, or pharmaceutical formulation thereof and reagents to prepare a composition for administration. The composition can be in a dry or lyophilized form, or in a solution, particularly a sterile solution. When the composition is in a dry form, the reagent can comprise a pharmaceutically acceptable diluent for preparing a liquid formulation. Such diluents include those known to those of skill in the art, for example, saline solutions such as PBS. In various embodiments, the lipid-containing composition can be, for example, any of the lipid compositions described herein or known in the art for the preparation of lipid-encapsulating vesicles.

When in a wet form, the diluent/buffer and/or the reconstituted blood substitute composition as described herein can be stored in a blood bag or other sterile sealed container, including those known to persons of skill in the art.

The kits can include other therapeutic compounds for use in conjunction with the compounds described herein. In one embodiment, the therapeutic agents are other agents useful in treating conditions that would necessitate transfusion with blood or a blood substitute. These agents can be provided in a separate form, or mixed with the compositions described herein, provided such mixing does not reduce the effectiveness of either the additional therapeutic agent or the compositions and formulations described herein. By way of non-limiting examples, such agents include, antihemorrhagic drugs, either or both hemostatic and/or styptic, such as for example antifininolutics, vitamin K, fibrinogen, and blood coagulation factor, and kaolin; prophylactic antibiotics, acetaminophen, NSAIDs, hydroxyurea (Droxia, Hydrea), chemotherapy, blood transfusion, and platelet transfusion.

Kits can further comprise suitable packaging and/or instructions for use of the composition. Kits can also comprise a means for the delivery for the composition, or pharmaceutical formulation thereof, such as, for example, an intravenous needle, blood transfusion tubing, syringe for injection or other device as described herein and known to those of skill in the art.

The kits can include appropriate instructions and information for preparation and administration of the composition, side effects of the compositions, and any other relevant information. The instructions can be in any suitable format, including, but not limited to, printed matter, videotape, computer readable disk, or optical disc.

Kits can also be provided that contain sufficient dosages of the compositions or formulations thereof as disclosed herein to provide effective treatment for an individual for an extended period, such as a week, 2 weeks, 3, weeks, 4 weeks, 6 weeks, 8 weeks, 3 months, 4 months, 5 months, 6 months, 7 months, 8 months, 9 months or more.

Some embodiments of the present invention can be defined as any of the following paragraphs:

A lipid vesicle comprising hemoglobin, an oxido-reductase enzyme, a dismutase, a catalase, a reducing agent, and an electron acceptor.

The vesicle of paragraph 159, wherein the oxido-reductase enzyme, is DT-diaphorase.

The vesicle of paragraph 159, wherein the dismutase is a superoxide dismutase.

The vesicle of paragraph 159, wherein the reducing agent is NADH, or NADPH.

The vesicle of paragraph 159, wherein the electron acceptor is methylene blue.

The vesicle of paragraph 159, further comprising a physiological saline solution.

The vesicle of paragraph 159, wherein the physiological saline solution is PBS.

The vesicle of paragraph 159, wherein the hemoglobin concentration within the vesicle is 5-15 g/dL inclusive.

The vesicle of paragraph 159, wherein the hemoglobin concentration within the vesicle is comprised between 6.5-10 g/dL inclusive.

The vesicle of paragraph 159, wherein the hemoglobin concentration within the vesicle is comprised between 6.5-8 g/dL inclusive.

The vesicle of paragraph 159, wherein the hemoglobin concentration within the vesicle is comprised between 7.0-7.9 g/dL inclusive.

The vesicle of paragraph 159, wherein the hemoglobin concentration within the vesicle is comprised between 7.25-7.75 g/dL inclusive.

The vesicle of paragraph 159, wherein the hemoglobin concentration within the vesicle is 7.5 g/dL.

The vesicle of paragraph 159, wherein the vesicle size is comprised between 150 nm to 500 nm inclusive.

The vesicle of paragraph 159, wherein the vesicle size is comprised between 180 nm to 220 nm inclusive.

The vesicle of paragraph 159, wherein the vesicle size is 200 nm.

The vesicle of paragraph 159, wherein the lipid vesicles comprises at least one lipid selected from the group consisting of: DPPC (1,2-dipalmitoyl-sn-glycero-3-phosphocholine), DSPC (1,2-distearoyl-sn-glycero-3-phosphocholine), DOPC (1,2-dioleoyl-sn-glycero-3-phosphocholine), DLPC (1,2-dilauroyl-sn-glycero-3-phosphocholine), DPPG (1,2-dipalmitoyl-sn-glycero-3-[phospho-rac-(3-lysyl(1-glycerol))]), DSPG (1,2-distearoyl-sn-glycero-3-phospho-(1'-rac-glycerol)), DHPG (3,5-Dihydroxyphenylglycine), DOPG (1,2-dioleoyl-sn-glycero-3-[phospho-rac-(3-lysyl(1-glycerol))]), DSPEG PEG 5000 (1,2-distearoyl-sn-glycero-3-phosphoethanolamine-N-[folate(polyethylene glycol)-5000]), DSPE-PEG200 (1,2-distearoyl-sn-glycero-3-phosphoethanolamine-N-[maleimide(polyethylene glycol)-2000]), and DOPE-PEG5000 (1,2-dioleoyl-sn-glycero-3-phosphoethanolamine).

The vesicle of paragraph 159, wherein the lipid vesicles comprises: Cholesterol, DPPC, DSPE-PEG5000, and DPPG.

The vesicle of paragraph 176, wherein the ratio of Cholesterol, DPPC, DSPE-PEG5000, and DPPG is respectively 5:5:0.0333:1.

A suspension comprising lipid vesicles of any one of paragraph 159 through paragraph 177, wherein the lipid vesicles are suspended in a physiological saline solution.

The suspension of claim of paragraph 178, wherein the physiological saline solution is PBS.

The suspension of claim paragraphs 177 or 178 wherein the physiological saline solution comprises a reducing agent.

The suspension of claim paragraph 180 wherein the reducing agent is NADH or NADPH.

The suspension of paragraphs 178-181, wherein the concentration of vesicles in the suspension is comprised between $10^{15}$ to $10^{17}$ vesicles/ml inclusive.

A method of encapsulating a blood substitute composition, the method comprising the steps of:
Group a. mixing a lipid preparation with a composition comprising an oxido-reductase enzyme, a dismutase, a catalase, a reducing agent, and an electron acceptor;
Group b. extruding the mixture to form lipid vesicles; and
Group c. isolating lipid vesicles.

The method of paragraph 183, wherein the oxido-reductase enzyme comprises DT-diaphorase.

The method of paragraph 183, wherein the dismutase comprises superoxide dismutase.

The method of paragraph 183, wherein the reducing agent comprises NADH or NADPH.

The method of paragraph 183, wherein the electron acceptor comprises methylene blue.

The method of paragraph 183, wherein the lipid preparation comprises at least one lipid selected from the group consisting of: DPPC, DSPC, DOPC, DLPC, DPPG, DSPG, DHPG, DOPG, DSPEG PEG 5000, DSPE-PEG200, and DOPE-PEG5000.

The method of paragraph 188, wherein the lipid preparation comprises:
  Group a. at least one lipid selected from the group consisting of: DPPC, DSPC, DOPC, and DLPC;
  Group b. at least one lipid selected from the group consisting of: DPPG, DSPG, DHPG, and DOPG; and
  Group c. at least one lipid selected from the group consisting of: DSPEG PEG 5000, DSPE-PEG200, and DOPE-PEG5000.

The method of paragraph 183, wherein the size of the isolated vesicles is comprised between 150 nm to 500 nm inclusive The method of paragraph 183, wherein the size of the isolated vesicles is comprised between of 180 nm to 220 nm inclusive.

The method of paragraph 183, wherein the size of the isolated vesicles is 200 nm.

The method of paragraph 183, wherein the lipid preparation comprises: Cholesterol, DPPC, DSPE-PEG5000, and DPPG.

The method of paragraph 193, wherein the ratio of Cholesterol, DPPC, DSPE-PEG5000, and DPPG is respectively 5:5:0.0333:1.

A method of reducing methemoglobin to hemoglobin in a vesicle, the method comprising: contacting methemoglobin with a composition comprising: an oxido-reductase enzyme, a dismutase, a catalase, a reducing agent, and an electron acceptor.

The method of paragraph 195, wherein the vesicle is in vitro.

The method of paragraph 195, wherein the vesicle is in vivo.

A kit comprising:
  Group a. a first container comprising: hemoglobin, an oxido-reductase enzyme, a dismutase, a catalase, a reducing agent, and an electron acceptor; and
  Group b. a second container comprising a lipid preparation.

The kit of paragraph 198, wherein the oxido-reductase enzyme comprises DT-diaphorase.

The kit of paragraph 198, wherein the dismutase comprises superoxide dismutase.

The kit of paragraph 198, wherein the reducing agent comprises NADH or NADPH.

The kit of paragraph 198, wherein the electron acceptor comprises methylene blue.

The kit of paragraph 198, wherein the lipid preparation comprises:
  Group a. at least one lipid selected from the group consisting of: DPPC, DSPC, DOPC, and DLPC;
  Group b. at least one lipid selected from the group consisting of: DPPG, DSPG, DHPG, and DOPG; and
  Group c. at least one lipid selected from the group consisting of: DSPEG PEG 5000, DSPE-PEG200; and DOPE-PEG5000.

A kit comprising:
  Group a. a first container comprising lipid vesicles comprising hemoglobin, an oxido-reductase enzyme, a dismutase, a catalase, and an electron acceptor;
  Group b. and a second container comprising a reducing agent, and a phosphate buffered saline.

The kit of paragraph 204, wherein the oxido-reductase enzyme comprises DT-diaphorase.

The kit of paragraph 204, wherein the dismutase comprises superoxide dismutase.

The kit of paragraph 204, wherein the reducing agent comprises NADH or NADPH.

The kit of paragraph 204, wherein the electron acceptor comprises methylene blue.

The kit of paragraph 204, wherein the phosphate buffered saline is PBS.

A kit comprising:
  Group a. a first container comprising lipid vesicles comprising hemoglobin, an oxido-reductase enzyme, a dismutase, a catalase, and an electron acceptor;
  Group b. a second container comprising a reducing agent;
  Group c. a third container comprising a phosphate buffered saline.

The kit of paragraph 210, wherein the oxido-reductase enzyme comprises DT-diaphorase.

The kit of paragraph 210, wherein the dismutase comprises superoxide dismutase.

The kit of paragraph 210, wherein the reducing agent comprises NADH or NADPH.

The kit of paragraph 210, wherein the electron acceptor comprises methylene blue.

The kit of paragraph 210, wherein the phosphate buffered saline is PBS.

A lipid vesicle of any one of paragraphs 159-177 for the treatment of blood loss.

A suspension of any one of paragraphs 178-182 for the treatment of blood loss.

The use of the vesicle of any one of paragraphs 159-177 for treatment of blood loss.

The suspension of any one of paragraphs 178-182 for treatment of blood loss.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefor, is not intended to limit the claimed processes to any order except as may be specified in the claims. Accordingly, the invention is limited only by the following claims and equivalents thereto.

EXAMPLES

Example 1

Lipid Vesicle Encapsulation Procedure

The following is a protocol for lipid vesicle encapsulation of a hemoglobin preparation as described herein.

Dissolve Cholesterol, DPPC, DSPE-PEG5000, and DPPG in chloroform appropriate concentrations (10 mg/ml) to make the stocks. As shown in Table 1, prepare a 20 ml vial dried with chloroform using pre-cleaned Avanti needles. Make the mixture of lipids at a ratio of 5:5:0.0333:1.

TABLE 1

The lipids used in the formation of vesicles and their characteristics.

| Lipid Type | Molar ratio | mol % | Solution (mg/mL) | MW (g/mol) | % by Weight |
|---|---|---|---|---|---|
| Cholesterol | 5 | 45.3 | 10 | 386.66 | 0.2955373 |
| DPPC | 5 | 45.3 | 10 | 734.039 | 0.5610509 |
| DSPE-PEG500 | 0.0333 | 0.3 | 10 | 5801.71 | 0.0295334 |
| DPPG | 1 | 9.1 | 10 | 744.952 | 0.1138784 |

Heat samples (hemoglobin preparation and PBS control) at 40° C. for 30 minutes while making the above mixture. Dry mixture of lipids with gently pressurized air in a rotary motion using a syringe and 5 seconds of exposure to 40 degree heat on the hotplate to completely evaporate off chloroform. This should leave only a circular mixture of the lipids in the desired ratios without chloroform at the bottom of the flask. Add 2 ml of sample (hemoglobin preparation and PBS) to the lipid mixture and vortex for 1 minute. Let this mixture sit in a 40° C. water bath for 1 hour.

Use extruder with appropriate membrane 21 times at 40° C. to get vesicles at the appropriate size. Typically, 0.2 μm filters yield 200 nm particles. Store overnight at 4° C. Next day centrifuge the sample through 100 kDa filters at 1500 rpm for 2 hours. Typically, 1 ml of sample remains after the centrifugation. Setup agarose gel column using PD-10 disposable columns (Sigma Aldrich). Sepharose® CL-4B beads were used in this separation procedure. Some of the characteristics of the beads include bead diameter 40-165 μm and pore size 30,000-5,000,000 fractionation range (dextrans) 60,000-20,000,000 fractionation range (globular proteins).

As hemoglobin tends to adhere to the column, first run PBS through. Take samples at 5 drops/well in 96 well plates. The encapsulated sample is the cloudy mixture. Use Dynamic Light Scattering particle sizer to determine which wells contain the sample at 200 nm with high sample quality. Pool the wells and store sample for further experiments at 4° C.

Example 2

Characterization of Individual Artificial Blood Constituents

Each component present in the hemoglobin preparation is important to the stability of the hemoglobin. The following experiment was conducted to assess the functions of NADH, DT-Diaphorase, methylene blue, superoxide dismutase, and catalase by excluding each component individually and taking the UV absorbance to confirm the stability of oxyhemoglobin. FIGS. 1A-1H show the importance of the individual components of the hemoglobin preparation in keeping the hemoglobin in a reduced form and thus preventing conversion to methemoglobin. Oxyhemoglobin (FIG. 1A) has a distinct UV absorbance curve where sharp peaks are observed at around 450, 540 nm and 580 nm. Methemoglobin (FIG. 1B) however, has a drastically different curve with a less steep slope and has lesser peaks around 630 nm, 575, and broad peak from 450 nm to 530 nm. One can analyze whether or not there is methemoglobin present based on these characteristics of the peak. The increase of amplitude of the peaks and hence increased areas under the curve suggests greater concentrations of the reagents of interest. As each component is sequentially removed, the physiochemical state of hemoglobin can be inferred from the absorbance plots. Removing DT-diaphorase (FIG. 1C) causes a slight decrease in oxyhemoglobin, seen as a decrease in amplitude in the UV absorbance curves. Although exclusion of DT-diaphorase does not halt the chemical reaction, it reduces the reaction rate. Removing methylene blue (FIG. 1D) causes some oxyhemoglobin to revert to methemoglobin, as seen by a sharp absorbance increase at 540 nm and 580 nm. This suggests that the solution contains both methemoglobin and hemoglobin. As methylene blue catalyzes this reaction, its exclusion limits the rate of oxyhemoglobin production and hence increases the residual levels of methemoglobin. Removing NADH (FIG. 1E) causes the formation of methemoglobin because it is one of the active substrates in the reduction reaction, as seen as a methemoglobinlike characteristic curve. Finally, removing Super Oxide Dismutase (FIG. 1G), catalase (FIG. 1H) or both (FIG. 1F) at the same time causes no difference in peaks observed compared to the hemoglobin preparation positive control. In conclusion, methylene blue and NADH are critical chemicals in preventing the hemoglobin from converting to methemoglobin while diaphorase increases the concentration of oxyhemoglobin and the other components (Super Oxide Dismutase and Catalase) do not have any role in the reduction mechanism. However, this experiment does not prove that these are unnecessary chemicals. They fulfill another role in the stability of the hemoglobin preparation that primarily involves preventing free radical formation.

Example 3

Preventing NO Scavenging

Nitric Oxide (NO) scavenging prevention is an important aspect of this blood substitute. Nitric oxide plays an important role in blood pressure regulation and thus has a dramatic effect on oxygen delivery. The prevention of NO scavenging causes an increase in efficient oxygen delivery to vital tissue in the body. The NO scavenging assay was performed using the OxiSelect® In Vitro ROS/RNS Assay Kit (Green Fluorescence) kit. FIG. 2 shows nitric oxide scavenging between the different samples. These data shows that unencapsulated PBS and encapsulated PBS show no difference in NO levels. However, there is a substantial difference observed between the NO levels of the unencapsulated hemoglobin-based blood substitute (HBBS) and the encapsulated HBBS. A similar trend is observed between the unencapsulated methemoglobin and the encapsulated methemoglobin. Encapsulation of the hemoglobin prevents the thiol groups in hemoglobin from binding Nitric oxide and keeping it in solution. A higher value of nitric oxide in solution indicates lesser amounts of nitric oxide scavenging.

The invention claimed is:
1. A method of encapsulating a blood substitute composition, the method comprising the steps of:
  a. mixing a lipid preparation with a composition comprising an oxido-reductase enzyme, a dismutase, a catalase, a reducing agent, and an electron acceptor;
  b. extruding the mixture to form lipid vesicles; and
  c. isolating lipid vesicles, wherein the lipid preparation comprises at least one lipid selected from the group consisting of: DPPC, DSPC, DOPC, DLPC, DPPG, DSPG, DHPG, DOPG, DSPEG PEG 5000, DSPE-PEG200, and DOPE-PEG5000,
  and, wherein electron acceptors include but are not limited to: methylene blue, sodium 2,6-dibromophenol-indophenol, sodium 2,6-dichlorophenol-indophenol, sodium o-cresol indophenols, indigotetrasulfonic acid, indigotrisulfonic acid, indigo carmine, indigomono sulfonic acid, phenosafranin, safranin T, neutral red, and thionine.
2. The method of claim 1, wherein the oxido-reductase enzyme comprises DT-diaphorase.

3. The method of claim 1, wherein the dismutase comprises superoxide dismutase.

4. The method of claim 1, wherein the reducing agent comprises NADH or NADPH.

5. The method of claim 1, wherein the electron acceptor comprises methylene blue.

6. The method of claim 1, wherein the lipid preparation comprises:
   a. at least one lipid selected from the group consisting of: DPPC, DSPC, DOPC, and DLPC;
   b. at least one lipid selected from the group consisting of: DPPG, DSPG, DHPG, and DOPG; and
   c. at least one lipid selected from the group consisting of: DSPEG PEG 5000, DSPE-PEG200, and DOPE-PEG5000.

7. The method of claim 1, wherein the size of the isolated vesicles is comprised between 150 nm to 500 nm inclusive.

8. The method of claim 1, wherein the size of the isolated vesicles is comprised between of 180 nm to 220 nm inclusive.

9. The method of claim 1, wherein the size of the isolated vesicles is 200 nm.

10. The method of claim 1, wherein the lipid preparation comprises: Cholesterol, DPPC, DSPE-PEG5000, and DPPG.

11. The method of claim 10, wherein the ratio of Cholesterol, DPPC, DSPE-PEG5000, and DPPG is respectively 5:5: 0.0333:1.

* * * * *